(12) United States Patent
Uchegbu et al.

(10) Patent No.: US 7,741,474 B2
(45) Date of Patent: Jun. 22, 2010

(54) SOLUBILISING POLYSACCHARIDES SUBSTITUTED WITH DYDROPHILIC AND HYDROPHOBIC GROUPS

(75) Inventors: Ijeoma Uchegbu, Glasgow (GB); Andreas Schatzlein, Glasgow (GB); Ailsa Stewart, Hove (GB); Clive Wilson, Glasgow (GB)

(73) Assignee: The School of Pharmacy, University of London, London (GB)

( * ) Notice: Subject to any disclaimer, the term of this patent is extended or adjusted under 35 U.S.C. 154(b) by 908 days.

(21) Appl. No.: 10/528,603

(22) PCT Filed: Sep. 22, 2003

(86) PCT No.: PCT/GB03/04062

§ 371 (c)(1),
(2), (4) Date: Sep. 29, 2005

(87) PCT Pub. No.: WO2004/026912

PCT Pub. Date: Apr. 1, 2004

(65) Prior Publication Data

US 2006/0167116 A1 Jul. 27, 2006

(30) Foreign Application Priority Data

Sep. 20, 2002 (GB) .................................. 0221941.8

(51) Int. Cl.
C08B 37/00 (2006.01)
C07H 5/04 (2006.01)
C07H 5/06 (2006.01)

(52) U.S. Cl. .................... 536/55.2; 536/55.1; 536/123.1

(58) Field of Classification Search ........................ None
See application file for complete search history.

(56) References Cited

U.S. PATENT DOCUMENTS

| 4,436,731 A | 3/1984 | Maltz |
| 5,300,494 A | 4/1994 | Brode, II et al. |

FOREIGN PATENT DOCUMENTS

| CA | 2092513 | 9/1993 |
| DE | 0 563 013 | 9/1993 |
| EP | 0 544 000 | 2/1993 |

OTHER PUBLICATIONS

Kotze et al. Journal of Controlled Release (1998), vol. 51, pp. 35-46.*
Kubota et al. Carbohydrate Research (2000), vol. 324, pp. 268-274.*
Schipper et al. Pharmaceutical Research (1997), vol. 14, pp. 923-929.*
Wang et al. Langmuir (2001), vol. 17, pp. 631-636.*
Laschewsky, A., *Molecular concepts, self-organisation and properties of polysoaps*. Advances in Polymer Science, 124: 1-86 (1995).
Yang, Y.J. and J. Engberts, *Preparation and Stability of Polystyrene Latexes Using Polysoaps as Emulsifiers*, European Polymer Journal, 28: 881-886 (1992).
Anton, P. and Laschewsky, A., *Solubilization by Polysoaps*. Colloid and Polymer Science, 272: 1118-1128 (1994).
Yang, Y.J. and Engberts, J., *Fluorescence Spectroscopic Study of the Formation of Hydrophobic Microdomains in Aqueous-solutions of Poly(Alkylmethyldiallylammonium Bromides)*. Recueil Des Travaux Chimiques Des Pays-Bas-Journal of the Royal Netherlands Chemical Society, 110: 384-386 (1991).
Cochin, D., Candau, F., Zana, R. and Talmon, Y., *Direct Imaging of Microstructures Formed in Aqueous-Solutions of Polyamphiphiles*. Macromolecules, 25: 4220-4223 (1992).
Binana-Limbele, W., Zana, R., *Fluoresence Probing of Microdomains in Aqueous-Solutiosn of Polysoaps .2. Study of the Size of the Microdomains*. Macromolecuels, 23: 2731-2739 (1990).
Yoshioka, H., Nonaka, K., Fukuda, K., and Kazama, S., *Chitosan-Derived Polymer-Surfactants and Their Micellar Properties*. Bioscience Biotechnology and Biochemistry, 59: 1901-1904 (1995).
Gautier, S., Boustta, M., Vert, P. *Alkylated poly(L-lysine citramide) as models to investigate the ability of amphiphilic macromolecular drug carriers to physically entrap lipophilic compounds in aqueo9us media*. Journal of Controlled Release, 60: 235-247 (1999).
Miwa, A., Ishibe, A., Nakano M., Yamahira, T., Itai, S., Jinno, S., Kawahara, H., *Development of novel chitosan derivatives as micellar carriers of taxol*. Pharmaceutical Research, 15: 1844-1850 (1998).
Kjoniksen, A.L., Nystrom, B., Iversen, C., Nakken, T., Palmgren, O., and Tande, T., *Viscosity of dilute aqueous solutions of hydrophobically modified chitosan and its unmodified analogue at different concentrations of salt and surfactant concentrations*. Langmuir, 13: 4948-4952 (1997).

(Continued)

*Primary Examiner*—Patrick T Lewis
(74) *Attorney, Agent, or Firm*—Saliwanchik, Lloyd & Saliwanchik

(57) ABSTRACT

This invention relates to novel carbohydrate polymers with hydrophobic and hydrophilic side-groups suitable for solubilising, for example, hydrophobic drugs. The chain length of the carbohydrate polymeric backbone, and the type and number of the hydrophobic and hydrophilic side-groups are specifically chosen to improve the solubility properties of the carbohydrate polymers.

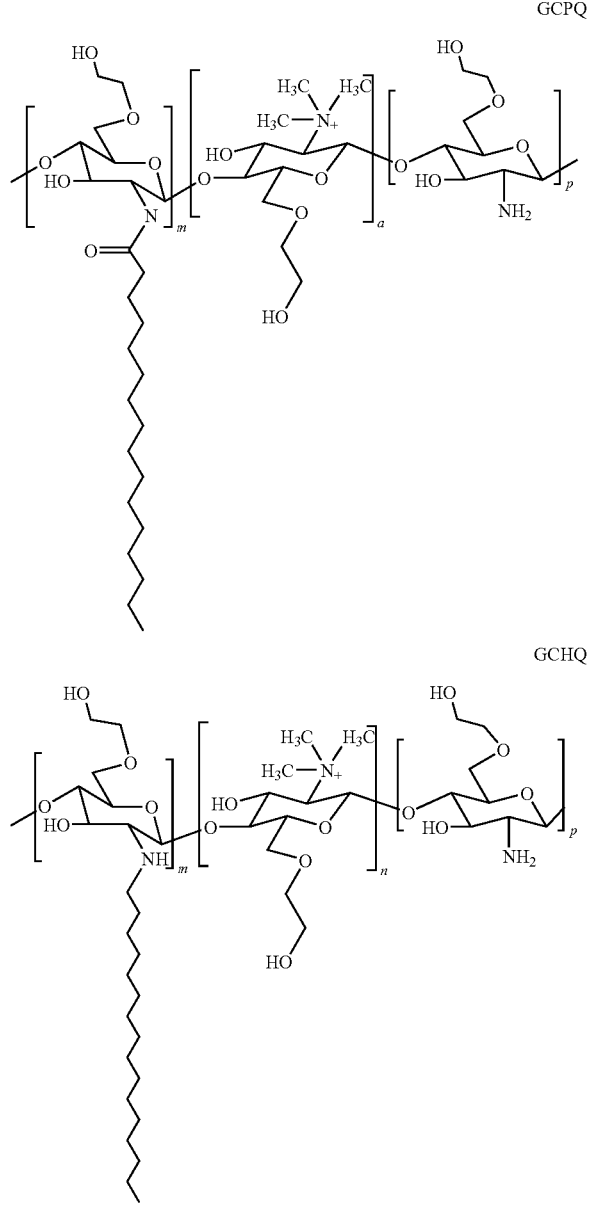

OTHER PUBLICATIONS

Kjoniksen, A.L., Iversen, C., Nystrom, B., Nakken, T., Palmgren, O., *Light scattering study of semidilute aqueous systems of chitosan and hydrophobically modified chitosans*. Macromolecules, 31: 8142-8148 (1998).

Uchegbu, I.F., Schtzlein, A.G., Tetley, L., Gray, A.I., Sludden, J., Sidique, S., and Mosha, E., *Polymeric chitosan-based vesicles for drug delivery*. Journal of Pharmacy and Pharmacology, 50: 453-458 (1998).

Wang, W., McConaghy, A.M., Tetley, L. and Uchegbu, I.F., *Controls on polymer molecular weight may be used to control the size of palmitoyl glycol chitosan polymeric vesicles*. Langmuir, 17: 631-636 (2001).

Lee, K.Y., Jo, W.H., Kwon, I.C., Kim, Y.H., and Jeong, S.Y., *Physicochemical characteristics of self-aggregates of hydrophobically modified chitosans*. Langmuir, 14: 2329-2332 (1998).

Lee, K.Y., Kim, J.H., Kwon, I.C., and Jeong, S.Y., *Self-aggregates of deoxycholic acid modified chitosan as a novel carrier of adriamycin*. Colloid and Polymer Science, 278: 1216-1219 (2000).

Akiyoshi, K., Deguchi, S., Moriguchi, N., Yamaguchi, S. and Sunamoto, J., *Self-aggregates of hydrophobized polysaccharides in water, formation and characteristics of nanoparticles*. Macromolecules, 26: 3062-3068 (1993).

Akoyoshi, K. Kang, E.C., Kurumada, S., Sunamoto, J., Principi, T., and Winnik, F.M., *Controlled association of amphiphilic polymers in water: thermosensitive nanoparticles formed by self-assembly of hydrophobically modified pullulans and poly(N-isopropylacrylamides)*. Macromolecules, 33: 3244-3249 (2000).

Kumar, G., Bristow, J.F., Smith, P.J. and Payne, G.F., *Enzymatic gelation of the natural polymer chitosan*. Polymer, 41: 2157-2168 (2000).

Wesslen, K.B., and Wesslen, B., *Synthesis of amphiphilic amylose and starch derivatives*. Carbohydrate Polymers, 47: 303-311 (2002).

Zhang, J., Pelton, R. and Wagberg, L., *Aqueous biphase formation by mixtures of dextran and hydrophobically modified dextran*. Colloid and Polymer Science, 276: 476-482 (1998).

Kastner, U., Hoffmann, H., Donges, R. and Ehrler, R., *Hydrophobically and Cationically Modified Hydroxyethyl Cellulose and Their Interactions with Surfactants*. Colloids and Surfaces a-Physicochemical and Engineering Aspects, 82: 279-297 (1994).

Roberts, G.A.F., and Wood, F.A., *A study of the influence of structure on the effectiveness of chitosan as an anti-felting treatment for wool*. Journal of biotechnology, 89: 297-304 (2001).

Viswanathan, A., *Effect of degree of substitution of octenyl succinate starch on the emulsification activity on different oil phases*. Journal of Environmental Polymer Degradation, 7: 191-196 (1999).

Kim, Y.H., Gihm, S.H., and Park, C.R., *Structural characteristics of size controlled self aggregates of deoxycholic acid-modified chitosan and their application as a DNA delivery carrier*. Bioconjugate Chemistry, 12: 932-938 (2001).

Lapasin, R., Delorenzi, L., Pricl, S., and Torriano, G., *Flow properties of hydroxypropyl guar gum and its long-chain hydrophobic derivatives*. Carbohydrate Polymers, 28: 195-202 (1995).

Wakita, M. and Hashimoto, M., *Bilayer Vesicle Formation of N-Octadecylchitosan*. Kobunshi Ronbunshu, 52: 589-593 (1995).

Domard, A., Rinaudo, M. and Terrassin, C.,*New method for the quaternisation of chitosan*. International Journal of Biological Macromolecules, 8: 105-107 (1986).

Uchegbu, I.F., Sadiq, L., Arastoo, M., Gray, A.I., Wang, W., Waigh, R.D., and Schtzlein, A.G., *Quartemary ammonium palmitoyl glycol chitosan- a new polysoap for drug delivery*. International Journal of Pharmaceutics, 224: 185-199 (2001).

Kalyanasundaram, K. and Thomas, J.K., *Environmental effects on the vibronic band intensities in pyrene monomer fluorescence and the application to studies of micellar systems*. Journal of the American Chemical Society, 99: 2039-204 (1977).

\* cited by examiner

20 Claims, 13 Drawing Sheets

SOLUBILISING POLYSACCHARIDES SUBSTITUTED WITH DYDROPHILIC AND HYDROPHOBIC GROUPS

FIELD OF THE INVENTION

This invention relates to novel carbohydrate polymers with hydrophobic and hydrophilic side-groups suitable for solubilising, for example, hydrophobic drugs. The chain length of the carbohydrate polymeric backbone, and the type and number of the hydrophobic and hydrophilic side-groups are specifically chosen to improve the solubility properties of the carbohydrate polymers.

BACKGROUND OF THE INVENTION

Soluble polymers bearing pendant amphiphilic or hydrophobic groups, commonly known as polysoaps, have been studied for a number of years and numerous applications proposed[1] based on exploiting their solubilisation capacity for hydrophobic molecules[2,3]. These compounds form intramolecular micelles[4,5], usually several per molecule[6], and their solubilisation capacity is not lost on dilution[1] unlike small molecular weight micelles[7], making them especially useful as solubilisers. Although these molecules are well known they have not been exploited to any great extent as pharmaceutical solubilisers.

Hydrophobic drugs are those drugs, which are practically insoluble in water. The definition of "practically insoluble" used by the British Pharmacopoeia is used here and is defined as a situation where 1 g of such material requires more than 10,000 millilitres of solvent (e.g. water) to be solubilised[8] or alternatively a material which has a solubility of less than 0.1 mg mL$^{-1}$ in water.

A few pharmaceutical solubilisers have been reported using hydrophobically and hydrophilically modified chitosans, namely: N-acyl 6-sulphated chitosans[10], quaternary ammonium palmitoyl glycol chitosan[8] and alkylated poly(L-lysine citramide)[11], although the effects of depolymerisation of the carbohydrate backbone was not explored in the work done on these carbohydrates[8,9,11]. However, two different molecular weights of N-lauroyl 6-carboxymethyl chitosan, with one molecular weight class being investigated at two different levels of lauroyl and carboxymethyl substitution, have been reported by Miwa and others[11] as "micellar" carriers of the hydrophobic drug paclitaxel. The paclitaxel formulation described by these workers however is prepared by the probe sonication of N-lauroyl 6-carboxymethyl chitosan and paclitaxel in a 10% v/v ethanol solution. The removal of ethanol by dialysis was attempted but not confirmed by these workers and final N-lauroyl 6-carboxymethyl chitosan—paclitaxel formulations were described as "turbid" with particle size ranges of between 30 and 300 nm and a mean particle size of between 32 and 82 nm. In contrast, the invention disclosed herein relates to the attributes of a solubilising polymer which produces optically clear solutions (devoid of appreciable light scattering) when hydrophobic drugs are added to an aqueous phase (devoid of organic solvents) in the presence of the solubilising polymer. Miwa and others on the other hand report that the precursor to N-lauroyl 6-carboxymethyl chitosan which contains no hydrophobic chain—carboxymethyl chitin "yielded a clear solution and the scattering phenomena detected in the case of micellar solution were not observed in the carboxymethyl chitin solution"[11]. The present invention thus differs from that reported by Miwa and others[11] in that an aqueous optically clear solution is prepared from the polymer and appropriate concentrations of poorly soluble drugs. Organic solvents are also not required in the preparation of the present solutions.

Hydrophobically modified chitosans soluble in dilute acid solutions have also been reported[12,13]. Other hydrophobically modified carbohydrates have been reported to yield particulate[14-19] dispersions in aqueous media as opposed to water soluble materials[13]—namely palmitoyl glycol chitosan[14,15], deoxycholic acid modified chitosan[16,17] and cholesterol bearing pullulans[18,19] or alternatively aqueous insoluble gel-like materials[20,21].

While the advantageous influence of depolymerisation, controlled hydrophilic substitution, and controlled hydrophobic substitution of carbohydrates on the production of an optically clear solution with hydrophobic drugs has not previously been described, reports on the individual influences of depolymerisation, hydrophobic substitution and hydrophilic substitution on polymer behaviour can be found in the literature. There is an indirect relationship between the length of hydrophobic pendant groups and water solubility in the case of hydrophobised starches[22] and hydrophobised ethyl celluloses[20]. This parameter also has a direct influence on the degree of polymer aggregation when in solution in the case of amphiphilic chitosans[9] and dextrans[23] as well as on the solubilising properties of hydrophobically modified chitosans[9]. The degree of hydrophobic substitution has also been reported to have an indirect influence on the aqueous solubility of starch derivatives[22] and affects the flow properties of hydroxypropyl guar gums.

The balance of hydrophobic and hydrophilic substitution has also been reported to affect a number of polymer properties. An increase in hydrophobic substitution from 20 substituents in every 100 monomers to 90 substituents in every 100 monomers with an associated decrease in the level of carboxymethyl substituents from 200 substituents in every 100 monomers to 140 substituents in every 100 monomers decreased the association of paclitaxel with the N-lauroyl 6-carboxymethyl chitosan colloids[11], indicating that a more hydrophobic polymer promoted association of paclitaxel with the chitosan based colloid. The balance between the level of hydrophobic and hydrophilic modification also affected the flow properties of amphiphilic hydroxyethylcelluloses[24] and an optimum hydrophobic modification level for amphiphilic chitosans has been identified when these materials are used to prevent wool shrinkage during washing[25].

With regard to amphiphilic polymer molecular weight alone this has been shown to have an indirect effect on the emulsifying activity of hydrophobised starches[26] and an optimum molecular weight has been identified for amphiphilic chitosans bearing deoxycholic acid pendant groups in the context of DNA—chitosan nanoparticles fabricated for gene delivery[27]. Also the molecular weight of hydrophobised (C6-acyl) dextrans influenced the phase separation of these systems with the high molecular weight material being more likely to phase separate[23]. The molecular weight of hydrophobic hydroxypropyl guar gums[28] was found to influence their flow properties. However, the molecular weight of N-lauroyl 6-carboxymethyl chitosan polymers did not affect their ability to encapsulate paclitaxel within the chitosan based colloid[11].

Returning to the work of Zhang and others on acyl dextrans[23], the main purpose of this work was to "prepare a family of polymer pairs in which the compatibility in aqueous solution could be varied in subtle ways" with a view to applying the results to the development of adhesives. The authors conclude that the tendency for dextran and hydrophobically modified dextran to phase separate increases with molecular weight, degree of hydrophobic substitution and hydrophobic chain length[23]. It should be noted that Zhang and others[23] did not explore the effect of molecular weight on the phase separation of hydrophobically and hydrophilically modified dextrans.

It is an object of embodiments of the present invention to obviate or mitigate at least one or more of the aforementioned problems.

It is a further object of embodiments of the present invention to provide a polymer for solubilising hydrophobic materials such as drugs.

SUMMARY OF THE INVENTION

According to a first aspect of the present invention there is provided a solubilising carbohydrate polymer of average molecular weight of about 2-30 kD according to the following formula:

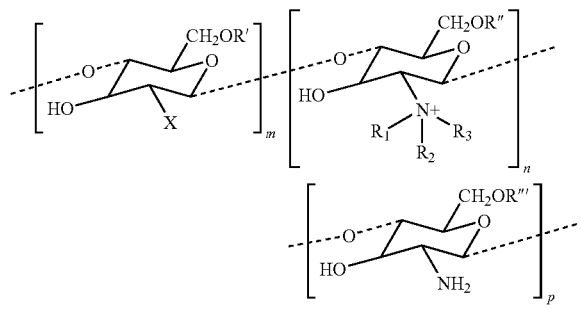

wherein m is 0.01% to 10.00%;
n is 0.01% to 99.98%;
p is 0.00% to 99.98%;
X is any linear or branched, substituted or unsubstituted, or cyclo form of an alkyl, alkenyl, alkynyl, aryl, amine, amide, alcohol or acyl group;
R', R", R''' are independently any linear or branched, substituted or unsubstituted, or cyclo form of an alkyl, alkenyl, alkynyl, aryl, amine, amide, alcohol, acyl group, any sugar substitutent or oligo polyoxa $C_1$-$C_3$ alkylene units; and
$R_1$, $R_2$ and $R_3$ are independently any linear or branched, substituted or unsubstituted, or cyclo forms of any alkyl, alkenyl, alkynyl, aryl or acyl group.

It is understood that m+n+p will be equal to 100%. It should also be understood that m, n and p may form any arrangement in the solubilising carbohydrate polymer. The arrangement of the m, n and p units may therefore be random or in a block copolymer form such as mnpmnpmnp etc. This is identified in the structure shown above by the dashed line between the different monomer units.

The carbohydrate polymer may be positively charged with a counter ion. The counter ion may be represented by any negative ion. Typically the counter ion may be ions of any of the following: chloride, iodide, acetate and glucoronide.

If the monomer unit identified by n is uncharged (i.e. the hydrophilic side group is uncharged) then the carbohydrate polymer may be uncharged and there will therefore be no counter ion.

Typically, X may be selected from any of the following linear or branched, substituted or unsubstituted, or cyclo groups: $C_1$-$C_{30}$; $C_8$-$C_{24}$; or $C_{12}$-$C_{18}$.

The X group may be selected from any of the following: any type of fatty acid derivative of, for example, stearic acid, oleic acid, palmitic acid; N-hydroxysuccinimide acid and any other activated acyl compounds; and anhydrides.

In particular, X may be $CH_3(CH_2)_{14}CONH$, or $CH_3(CH_2)_{15}NH$.

$R_1$, $R_2$ and $R_3$ may independently be any linear or branched, substituted or unsubstituted, or cyclo form of the following alkyl, alkenyl, alkynyl, aryl or acyl groups: $C_1$-$C_{30}$; $C_1$-$C_{12}$; $C_1$-$C_6$; or $C_1$.

Typically, $R_1$, $R_2$ and $R_3$ may be $C_1$-$C_4$ linear alkyl groups.
Conveniently, all of $R_1$, $R_2$ and $R_3$ may be $CH_3$.

On some monomers the C2 nitrogen may not be fully substituted and may be present as a secondary or tertiary amine.

R', R" and R''' may independently be any linear or branched, substituted or unsubstituted, or cyclo form of the following alkyl, alkenyl, alkynyl, aryl, amine, amide, alcohol or acyl groups: $C_1$-$C_{30}$; $C_1$-$C_{12}$; and $C_1$-$C_6$.

Typically, R', R" and R''' may be $C_1$-$C_4$ linear glycol based groups.

Typically, R', R" and R''' are any of the following sugar substituents: glucose, galactose, fructose and muramic acid.

R', R" and R''' may be oligo polyoxa $C_1$-$C_3$ alkylene units such as ethylene glycol oligomers.

All of R', R" and R''' may be $CH_2OCH_2CH_2OH$ or $CH_2CH_2OH$.

The carbohydrate polymer starting material to which additional hydrophobic and hydrophilic groups are attached may have an average molecular weight of about 2 to 30 kD. Preferably, the carbohydrate polymer starting material has a molecular weight of about 5 to 17 kD.

Conveniently, the X group may be hydrophobic.

Conveniently, the $R_1$, $R_2$ and $R_3$ groups form a quaternary ammonium group which is hydrophilic.

Hydrophilic groups are groups, which are well hydrated by water and associate on a molecular level with water. A further non-ionic hydrophilic group may replace $NR_1R_2R_3$, providing R', R" and R''' are equal to $CH_2O$-Y and Y is a hydrophilic substituent. In that case both hydrophilic substituents on the carbohydrate polymer may be selected from mono and oligo hydroxy C1-C6 alkyl, mono and oligo hydroxy substituted C2-C6 acyl, C1-C2 alkoxy alkyl optionally having one or more of the hydroxy groups substituted on the alkoxy or alkylene groups, oligo or poly-(oxa C1-C2 alkylene), preferably polyethylene glycol comprising up o 120 ethylene oxide units (i.e. a molecular weight of 5, 000), and C1-C4 alkyl (oligo or poly oxa C1-C3 alkylene) optionally hydroxy substituted preferably oligo or polyglycerol ethers; wherein the replacement group for $NR_1R_2R_3$ is joined via an ether linkage to a saccharide unit of the polysaccharide. The acyl group may contain alkyl, alkenyl or alkynyl groups.

The R', R" and R''' groups may also be hydrophilic.

Typically, the ratio of m:n:p may have the following range: 0.1:1:98.9 to 9:91:0; 1:5:96 to 8:50:42; or 3:10:87 to 5:19:76.

The total number of monomer units of m+n+p may be about 10 to 100. Preferably, the total number of monomer units of m+n+p may be less than about 200.

Typically, the number of X groups may not exceed 10 for every 100 monomer groups in the carbohydrate backbone.

The solubilising carbohydrate polymer may also contain additional targeting groups such as peptides, antibodies and other ligands, for example, folate and transferrin ligands which may allow the polymer to target endogenous receptors and thus target its drug payload to such endogenous receptors at the site of pathology.

According to a second aspect of the present invention there is provided a method of forming a solubilising carbohydrate polymer according to the first aspect wherein the method comprises;

depolymerising a carbohydrate polymer to form depolymerised carbohydrate;

reacting the depolymerised carbohydrate with a first reactive compound to form hydrophobic side-groups on the carbohydrate backbone and thus form hydrophobically substituted depolymerised carbohydrate; and adding a second reactive compound to the hydrophobically substituted depolymerised carbohydrate to quaternarise an amine group and thereby form the solubilising carbohydrate polymer.

The carbohydrate polymer may be selected from the following: glycol chitosans, dextrans, alginic acids, starches, dextran, guar gums and all other carbohydrate polymers.

The carbohydrate polymer may be depolymerised with any of the following: an acid, a base, or enzyme.

The acid used to depolymerise the carbohydrate polymer may be selected from any of the following: HCl, $H_2SO_4$, $HNO_3$ or HF.

The carbohydrate polymer may be depolymerised for a few days, for example, 48 hours, then isolated and subjected to further depolymerisation dependent on the average molecular weight of solubilising carbohydrate polymer required.

The average molecular weight of carbohydrate polymer to be depolymerised is about 3 to 30 kD and is preferably about 15 kD.

The first reactive compound which forms the hydrophobic side-groups on the depolymerised carbohydrate polymer may be selected from any of the following: any type of fatty acid derivative of, for example, stearic acid, oleic acid, palmitic acid; organo halides such as alkyl, alkenyl, alkynyl, cyclic or non-aromatic halides, acyl chlorides, anhydrides, N-hydroxysuccinimide and other activated acyl compounds capable of being attacked on the C1 carbon by a compound capable of nucleophilic attack. By nucleophilic attack is meant compounds which attack atoms with a low electron density. The acyl groups may also contain an alkyl, alkenyl or alkynyl group.

Preferably, the first reactive compound which forms the hydrophobic side-groups on the depolymerised glycol chitosan may be selected form any of the following: hexadecyl bromide, dodecyl bromide, myristic acid N-hydroxysuccinimide.

Preferably, the fatty acid derivative may be palmitic acid N-hydroxysuccinimide; palmitic acid benzotriazole carbonate; palmitaldehyde; palmitoyl chloride; and palmitic acid p-nitro phenyl carbonate.

The second reactive compound may be an organo halide wherein the organo may be selected from any linear or branch, substituted or unsubstituted, or cyclo form of any alkyl, alkenyl, alkynyl, aryl, amine, amide, alcohol or acyl group.

Typically, the second reactive compound may be any linear or branched, substituted or unsubstituted, or cyclo form of the following alkyl, alkenyl, alkynyl, aryl, amine, amide, alcohol or acyl groups: $C_1$-$C_{30}$; $C_1$-$C_{12}$; $C_1$-$C_6$; or $C_1$.

Typically, the organo group of the organo halides may be short chain linear alkyl groups.

The organo group of the organo halides may be $CH_3$.

The solubilising carbohydrate polymer obtained may be purified by column chromatography, dialysis and freeze drying.

According to a third aspect of the present invention there is provided a carbohydrate polymer according to the first aspect and a pharmaceutically acceptable carrier.

Pharmaceutically acceptable carriers are well known to those skilled in the art and include, but are not limited to, 0.1 M, or preferably 0.05 M phosphate buffer or 0.9% saline. Additionally, such pharmaceutically acceptable carriers may be aqueous or non-aqueous solutions, suspensions, and emulsions. Examples of non-aqueous solvents are propylene glycol, polyethyleneglycol, vegetable oils such as olive oil, and injectable organic esters such as ethyl oleate. Aqueous carriers include water, alcoholic/aqueous solutions, emulsions or suspensions, including saline and buffered media Parenteral vehicles include sodium chloride solution, Ringer's dextrose, dextrose and sodium chloride, lactated Ringer's or fixed oils. Preservatives and other additives may also be present, such as, for example, anti-microbial, anti-oxidants, chelating agents, inert gases and the like.

Typically, the ratio of carbohydrate polymer to pharmaceutical acceptable carrier ranges from 0.05 wt. % to 10 wt. %.

According to a fourth aspect of the present invention there is provided a pharmaceutical composition comprising a carbohydrate polymer according to a first aspect and a drug.

The drug may be poorly soluble in aqueous solvents such as water.

The drug may be selected from any of the following: prednisolone; cyclosporine; oestradiol, testosterone, drugs with multicyclic ring structures which lack polar groups such as paclitaxel and drugs such as etoposide.

Typically, the ratio of carbohydrate polymer to the drug may be 10 wt. % : 5000 wt. %.

Typically, the ratio of carbohydrate polymer to drug to pharmaceutically acceptable carrier may be about 1 mg:1-5 mg:1 g.

The pharmaceutical composition may be in the form of any of the following: tablets, suppositories, liquid capsule, powder form, or a form suitable for pulmonary delivery.

When tablets are used for oral administration, typically used carriers include sucrose, lactose, mannitol, maltitol, dextran, corn starch, typical lubricants such as magnesium stearate, preservatives such as paraben, sorbin, anti-oxidants such as ascorbic acid, α-tocopheral, cysteine, disintegrators or binders. When administered orally as capsules, effective diluents include lactose and dry corn starch. A liquid for oral use includes syrup, suspension, solution and emulsion, which may contain a typical inert diluent used in this field, such as water, in addition, sweeteners or flavours may be contained.

Suppositories may be prepared by admixing the compounds of the present invention with a suitable non-irritative excipient such as those that are solid at normal temperature but become liquid at the temperature in the intestine and melt in the rectum to release the active ingredient, such as cocoa butter and polyethyleneglycols.

The dose can be determined on age, body weight, administration time, administration method, combination of drugs, the level or condition of which a patient is undergoing therapy and other factors. While the daily doses may vary depending on the conditions and body weight of patients, the species or active ingredient, and administration route, in the case of oral use, the daily doses may be about 0.1-2 mg/person/day, preferably 0.5-100 mg/person/day.

According to a fifth aspect of the present invention there is provided a method of dissolving poorly soluble drugs in a carbohydrate polymer wherein the solubilising carbohydrate polymer has a specifically designed average molecular weight, and specific type and amount of hydrophilic and hydrophobic side-groups substituted on a carbohydrate polymeric backbone whereby on dissolving a poorly soluble drug in the solubilising carbohydrate polymer a substantially clear solution is obtained.

By substantially optically clear solution herein is meant an optically clear solution which is devoid of appreciable light scattering and is clear to the naked eye.

By poorly soluble drugs is meant where one gram of a drug requires more than 10,000 ml of solvent (water) to be solubilised. Alternatively, this means a drug which has a solubility of less than 0.1 mg mL$^{-1}$ in water.

Typically, the solubilising carbohydrate polymer is selected from any derivatives of the following: chitosans, dextrans, alginic acids, starches, dextran, guar gums and all other carbohydrate polymers.

In particular, the carbohydrate polymer according to the first aspect may be used.

The poorly soluble drug may be selected from any of the following: cyclosporin, steroids such as prednisolone, oestradiol, testosterone, drugs with multicyclic ring structures which lack polar groups such as paclitaxel and drugs such as etoposide.

BRIEF DESCRIPTION OF THE DRAWINGS

Embodiments of the present invention will now be described, by way of example only, with reference to the accompanying drawings in which.

EXAMPLES

Example 1

Materials

Figure 1A:
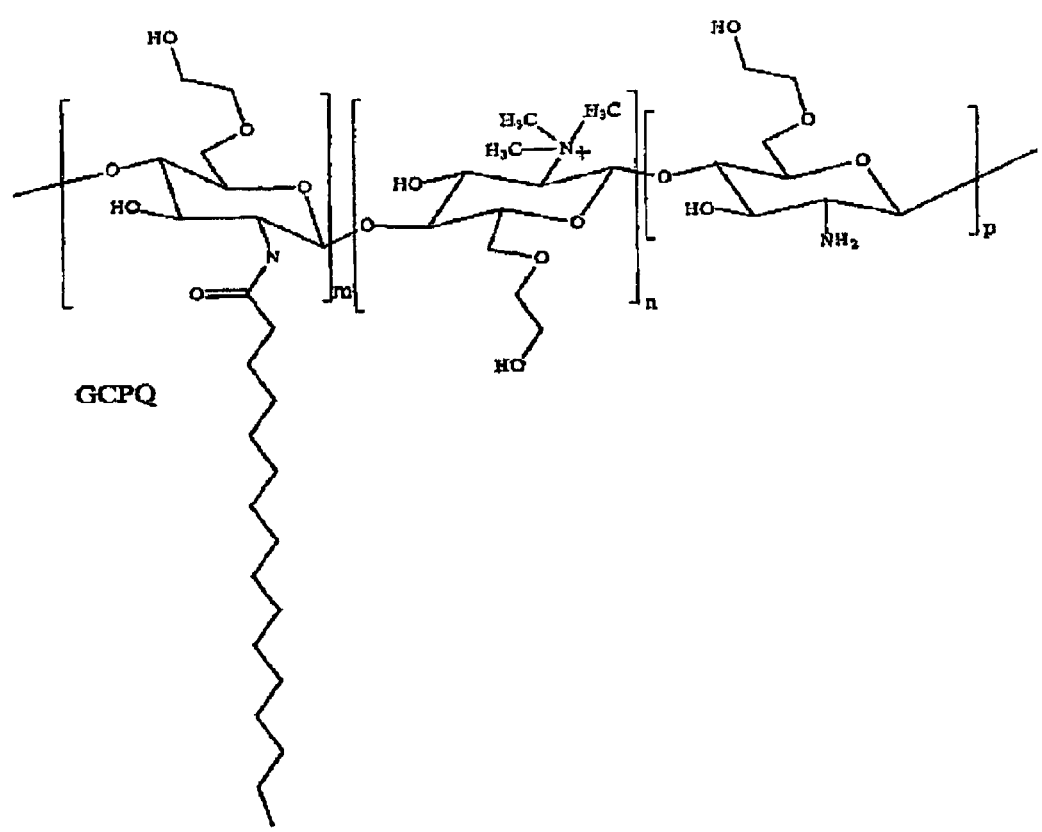
FIG. 1a is a representation of quaternary ammonium palmitoyl glycol chitosan (GCPQ)

Glycol chitosan, palmitic acid N-hydroxysuccinimde, methyl iodide, 1-bromohexadecane, pyrene and paclitaxel were all obtained from Sigma Aldrich Co, UK. Prednisolone acetate, prednisolone and cyclosporine were all obtained from Allergan, USA. Hydrochloric acid was obtained from Merck, UK and all organic solvents were purchased from the Department of Pure and Applied Chemistry, University of Strathclyde.

Methods

Degradation of Glycol Chitosan (GC)

Acid degradation of glycol chitosan (GC) was carried out as previously described[15]. Glycol chitosan (2 g) was dissolved in hydrochloric acid (4 M, 150 mL) and the solution filtered to remove insoluble impurities. The filtered solution was placed in a pre-heated water bath set at 50° C. After 48 h the reaction was stopped and the products isolated and purified as described below. The reaction solution was exhaustively dialysed (Visking Seamless Cellulose Tubing, molecular weight cut off=12,400 for cytochrome c) against distilled water (5 L with 6 changes over 24 h). The dialysate at the end of the dialysis procedure had a neutral pH. The dialysate was subsequently freeze-dried and the material was recovered as cream coloured cotton wool like material. The acid degradation step was repeated for either 4 h, 8 h, 24 h or 48 h to give materials, which were further depolymerised.

Synthesis of Low Molecular Weight Palmitoyl Glycol Chitosan (PGC)

Palmitoyl glycol chitosan (PGC) was synthesised as previously described[14]. Glycol chitosan (500 mg), sodium bicarbonate (376 mg) in a mixture of absolute ethanol (24 mL) and water (76 mL) was reacted with palmitic acid N-hydroxysuccinimide (198 mg) in absolute ethanol (150 mL). Palmitic acid N-hydroxysuccinimide solution was added dropwise. The product was isolated after stirring for 72 h by evaporating off most of the ethanol, extraction of the remaining liquid with three volumes of diethyl ether (100 mL), exhaustive dialysis against water and freeze dried to give a white cotton wool like solid.

Synthesis of Low Molecular Weight Hexadecyl Glycol Chitosan (GCH)

Hexadecyl glycol chitosan (GCH) was synthesised based on a modification of the method of Wakita and Hashimoto[29]. Glycol chitosan (500 mg) was dissolved in a 1:1 mixture of methanol and N-methyl pyrrolidinone (20 mL) and to this was added drop wise a solution of sodium bicarbonate (376 mg) dissolved in absolute ethanol (20 mL). 1-bromhexadecane (3.5 mL) was freshly dissolved in a mixture of methanol, N-methyl pyrrolidinone, absolute ethanol (5 mL:5 mL:10 mL) and this solution was added to the basic glycol chitosan solution drop wise over a 1 h time period. The resulting reaction mixture was refluxed at 70-85° C. in an oil bath with stirring over a period of 4 hours and then filtered and the filtrate retained. The ethanol was then evaporated off under reduced pressure at 50° C. and the residue produced dissolved in distilled water (30 mL). This solution was then dialysed against 5 L of water with 6 changes over 24 hours and freeze dried to give an off white solid.

Synthesis of Low Molecular Weight Quaternary Ammonium Palmitoyl Glycol Chitosan (GCPQ) and Low Molecular Weight Quaternary Ammonium Hexadecyl Glycol Chitosan (GCHQ)

Quaternisation was carried out using essentially the same method as reported by Domard and others[30]. PGC or GCH (300 mg) was dispersed in N-methyl-2-pyrrolidone (25 ml) overnight for 12 h at room temperature. Sodium hydroxide (40 mg), methyl iodide (1.0 g) and sodium iodide (45 mg) were added and the reaction stirred under a stream of nitrogen at 36° C. for 3 h. The quaternary ammonium product was recovered by precipitation with diethyl ether, filtered and washed with copious amounts of absolute ethanol followed by copious amounts of diethyl ether to give a brown hygroscopic solid. The solid was dissolved in water (100 ml) to give a yellow viscous solution. The resultant aqueous solution was exhaustively dialysed against water (5 L) with six changes over a 24 h period and the product freeze-dried to give a white cotton-like solid which was present as the iodide salt. The quaternary ammonium iodide was then dissolved in water (150 ml) to give a clear solution and the solution passed through a column (1×6 cm) packed with Amberlite IRA-93 Cl⁻. Before use the column was packed with resin and subsequently with one volume of the resin (30 ml) and subsequently washed with hydrochloric acid solution (90 ml, 1 M) followed by distilled water (500 ml) to give a neutral pH. The clear eluate from the column was freeze-dried to give GCPQ as a transparent fibrous solid.

¹H NMR

¹H NMR scans (with integration) and ¹H correlation spectroscopy experiments were performed on GCPQ and GCHQ samples solubilised in deuterated methanol and the level of palmitoylation and quaternisation determined by integrating the palmitoyl methyl, alkyl methyl or quaternary ammonium methyl peaks relative to the sugar peaks[31]. The mole % palmitoylation, alkylation or quaternisation refers to the number of moles of sugar monomers bearing a palmitoyl, alkyl or quaternary ammonium group per 100 moles of sugar monomers respectively.

MW Determination

The molecular weight of degraded glycol chitosan (GC) was determined by GPC-MALLS (i.e. gel permeation chromatography—multi angle laser light scattering). Polymers were dissolved in an acetate buffer (sodium acetate 0.3M, acetic acid 0.2M) and filtered (0.2 μm) samples (200 μL, 1-2 l mg mL⁻¹) injected onto GPC columns using a Waters 717 plus Autosampler. Samples were chromatographed over a PSS HEMA-BIO 300 (330×8 mm, particle size=10 μm, exclusion limit for dextran=5×10⁵) and a PSS HEMA-BIO 40 (330×8 mm, particle size=10 μm, exclusion limit for dextran=3×10⁶) column (Polymer Standards Services, Mainz, Germany). The mobile phase was an acetate buffer (sodium acetate 0.3M, acetic acid 0.2M) and molecular weights were determined using a DAWN EOS MALLS detector (18 angles at 20-150°—Wyatt Technology, USA) equipped with a 30 mV linearly polarized gallium arsenide laser ($\lambda$=690 nm) and an Optilab DSP interferometric refractometer ($\lambda$=690 nm, Wyatt Technology, USA). All the measurements were carried out at room temperature. Molecular weights, molecular weight distribution and molecular size in solution were obtained from GPC graphs using Astra for Windows (v4.73) software.

The refractive index increment (dn/dc) of GC in the mobile phase was measured with an Optilab DSP interferometric refractometer ($\lambda$=690 nm, Wyatt Technology, USA,) at 25° C. A Rheodyne 7725 sample injector was used to load filtered (0.45 μm) polymer solutions of various concentrations and the data were processed using DNDC for Windows (v5.31) software.

Fluorescence Spectroscopy

A dilute aqueous solution of pyrene (2 μM) was prepared by initially dissolving pyrene in ethanol (0.4 mg/mL). 100 μl of this solution was pipetted into a volumetric flask (100 mL) and the ethanol dried under a stream of nitrogen gas. The solution was then made up in distilled water. Using the aqueous pyrene solution as the solvent, polymer solutions were made at various concentrations. The fluorescence emission spectra were recorded (340 nm-600 nm) at an excitation wavelength of 335 nm. The $I_3/I_1$ ratio was calculated from the intensity of the third (383 nm) and first (375 nm) vibronic peaks in the pyrene emission spectra[32] and an increase in the size of the $I_3$ peak relative to the $I_1$ peak indicates a more hydrophobic environment[32]. In polar solvents such as water this value is approximately 0.67.

Solubilisation Studies

Various levels of the GCPQ and GCHQ samples were dissolved in water and a weighed amount of drug added with probe sonication (MSE Soniprep 150, Sanyo, UK with the instrument set at 60-85% of its maximum output) for about 5 minutes or until a clear solution is obtained. The presence of a clear solution was verified by optical density measurements ($\lambda$=600 nm, UV1 Spectrophotometer, ThermoUnicam, UK). The samples were stored at refrigeration (4-8° C.) or room (22° C.) temperature. At various time intervals liquid samples were filtered (0.45 μm, 25 mm in diameter) and the first millilitre discarded. The subsequent filtrate was retained and analysed for dissolved drug using HPLC.

Assay for Prednisolone

Prednisolone levels were analysed in filtered samples of the polymer—drug formulation by HPLC. Samples (20 μL), appropriately diluted with the mobile phase (acetonitrile, water 36:64) were injected onto a reverse phase Symmetry C18, 3.5 μm column (4.6 mm×755 mm, Waters Instruments, UK) by means of a Waters 717 autosampler and a Waters 515 isocratic pump. Peak detection was via a Waters 486 variable wavelength UV detector with the wavelength set at 243 nm and data was collected using a Waters 746 data module. The mobile phase was set at a flow rate of 1 ml min⁻¹. A standard curve was prepared with samples of prednisolone solubilised in the mobile phase (0.1-1.0 mg Ml⁻¹).

Assay for Cyclosporine

Cyclosporine was analysed by HPLC on the same instrumentation as above except that the column was a Waters Spherisorb 5 μm, 4.6 mm×250 mm column, maintained at 80° C. with a Jones Chromatography Column Heater model 7971. Filtered Samples (20 μL) dissolved in acetonitrile, water (1:1) were injected onto the column and the mobile phase was acetonitrile:water:tert-butyl-methyl-ether:phosphoric acid (600:350:50:1) at a flow rate of 1.2 mL min⁻¹. Peaks were detected by UV detection at a wavelength of 210 nm. A standard curve was prepared using solutions of the drug (1-10 μg mL⁻¹).

Haemocompatibilty Studies

Approximately 5 ml of human blood was centrifuged (1000 g×10 min), the supernatant removed and the erythrocyte pellet recovered. The pellet was washed twice by resuspending in PBS (pH 7.4, 4° C.) and centrifuging (1000 g×10 min). The pellet was then weighed and a 3% w/w dispersion of the erythrocytes was prepared in PBS (pH 7.4). 100 μL of this erythrocyte suspension was placed into each well of a 96 well plate. To this erythrocyte suspension was added 100 μL of varying concentrations of the sample formulations. Sample formulations were either prepared in phosphate buffered saline (PBS, pH=7.4) or water. PBS (pH=7.4) and Triton X-100 (1% w/v) served as negative and positive controls respectively. The plate was incubated at 37° C. for 4 h after which the plate was centrifuged (1000 g×10 min) and 100 μL of the supernatant removed and placed in a new microtitre plate. The absorbance was measured at 570 nm and the results expressed as percentage haemolysis assuming Triton X-100 gave 100% haemolysis and PBS (pH=7.4) gave 0% haemolysis.

Cytotoxicity Studies

A human lung carcinoma cell line (A549, ATCC CCL-185) and a human epidermoid carcinoma cell line (A431, ATCC CRL-1555) were both maintained in Dulbecco's minimum essential medium (DMEM) supplemented with 10% foetal calf serum (FCS) and 2 mM glutamine (GibcoBRL, U.K.) at 10% $CO_2$ and 37° C.

To measure the cytotoxicity of the formulations, a standard MTT (3-[4,5-dimethylthiazol-2-yl]2,5-diphenyltetrazolium bromide thiazolyl blue indicator dye) assay was carried out[33]. 96 well microtitre plates, 1 per formulation, were seeded with about 800 cells per well and incubated at 37° C. with 10% $CO_2$ for 72 hours. The medium was then removed from the wells and varying concentrations of each formulation (200 μL, prepared in 6% dextrose and diluted in medium) were added to the wells. DMEM alone and Triton X-100 (1% w/v) were used as positive and negative controls respectively. The plates were incubated under the standard conditions for 4 hours and the drug solutions then removed from the wells, replaced with DMEM and the cells further incubated for 72 hours. The indicator dye (50 μL, 50 mg $mL^{-1}$) was then added to the cells, which were subsequently incubated in the dark for a further 4 hours. At the end of the incubation time, the dye was removed and the cells lysed by addition of dimethylsulfoxide (200 μL). To the lysed cells was then added Sorensen's glycine buffer (25 μL) and the absorbance measured at 570 nm. Values are expressed as a percentage of the control minus the background obtained from the wells containing just DMEM.

Figure 1B:
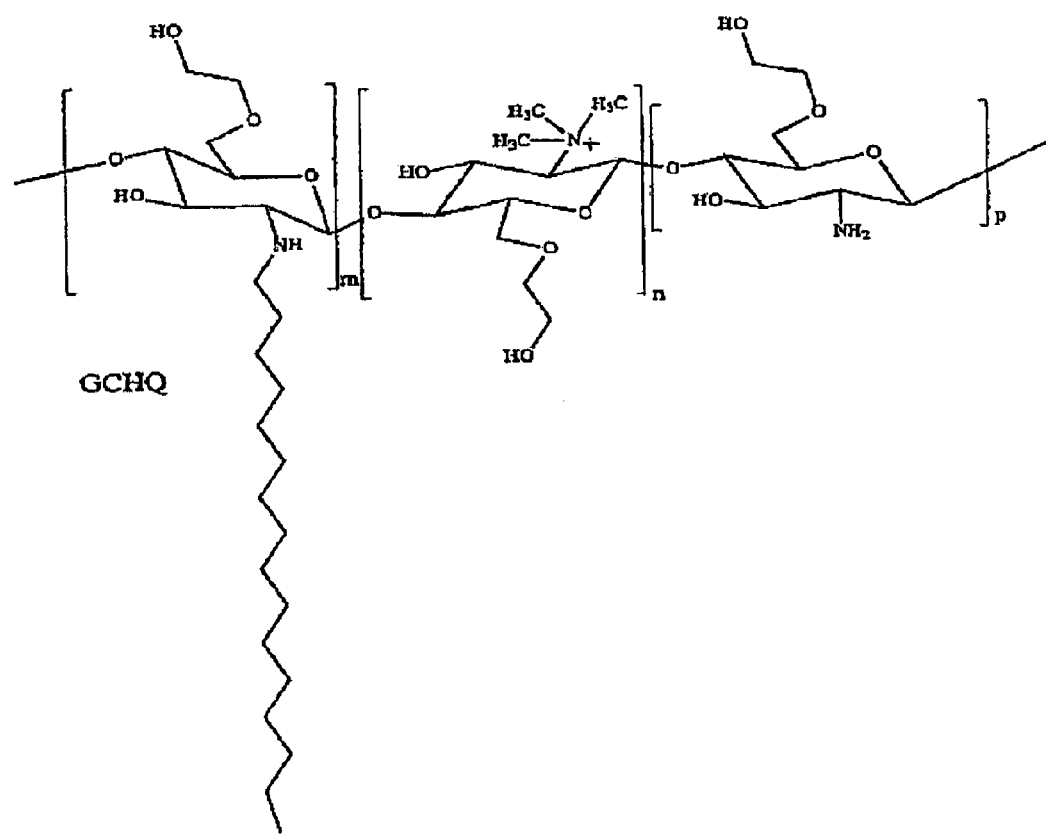
FIG. 1b is a representation of quaternary ammonium hexadecyl glycol chitosan (GCHQ)
Figure 2A:
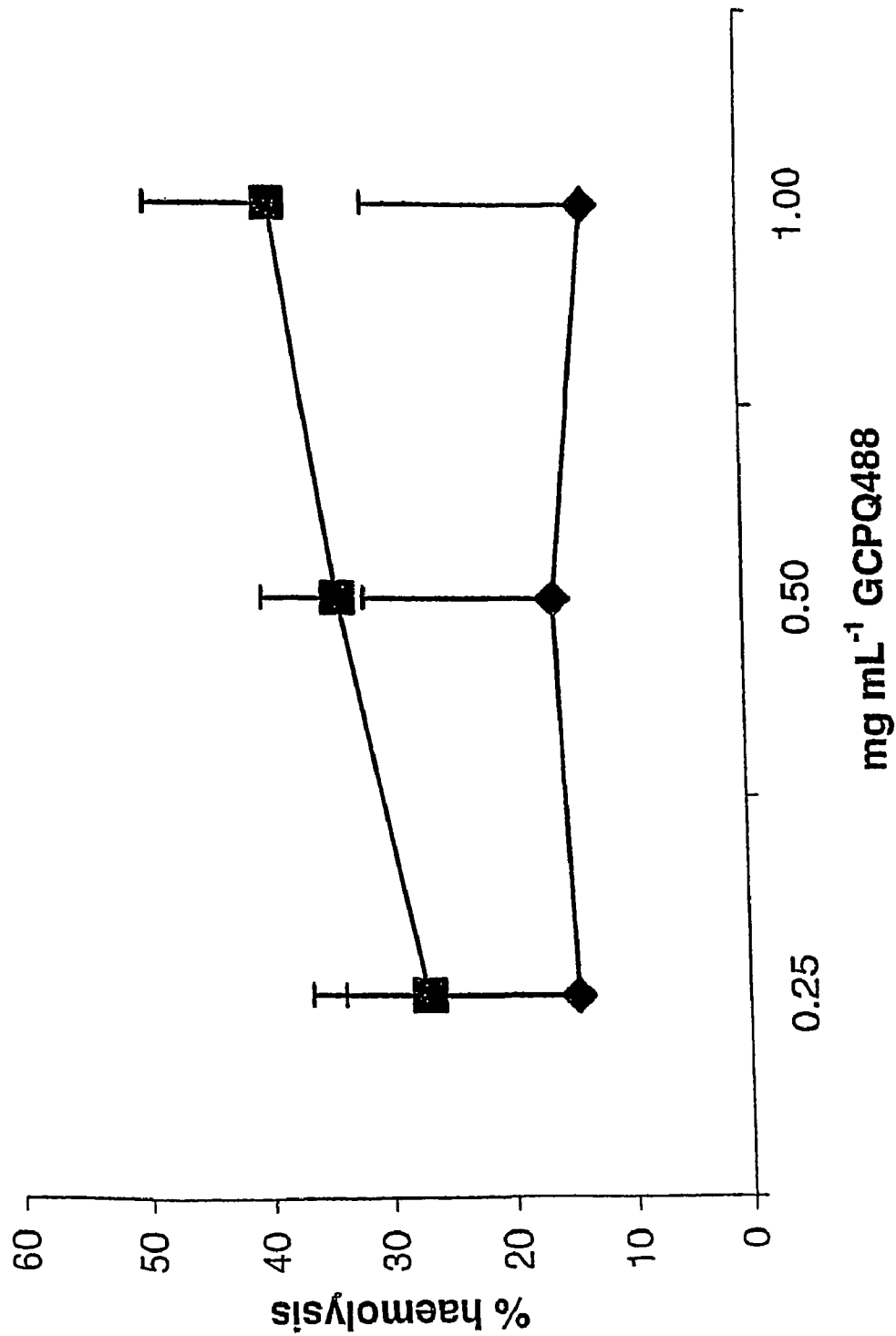
FIG. 2a is a representation of the haemolytic activity of GCPQ prepared from glycol chitosan which has been subjected to an initial 48 hours acid degradation and a further 8 hours acid degradation, followed by acylation with palmitic acid N-hydroxysuccinimide and alkylation with methyl iodide (i.e. GCPQ488)
Figure 2B:
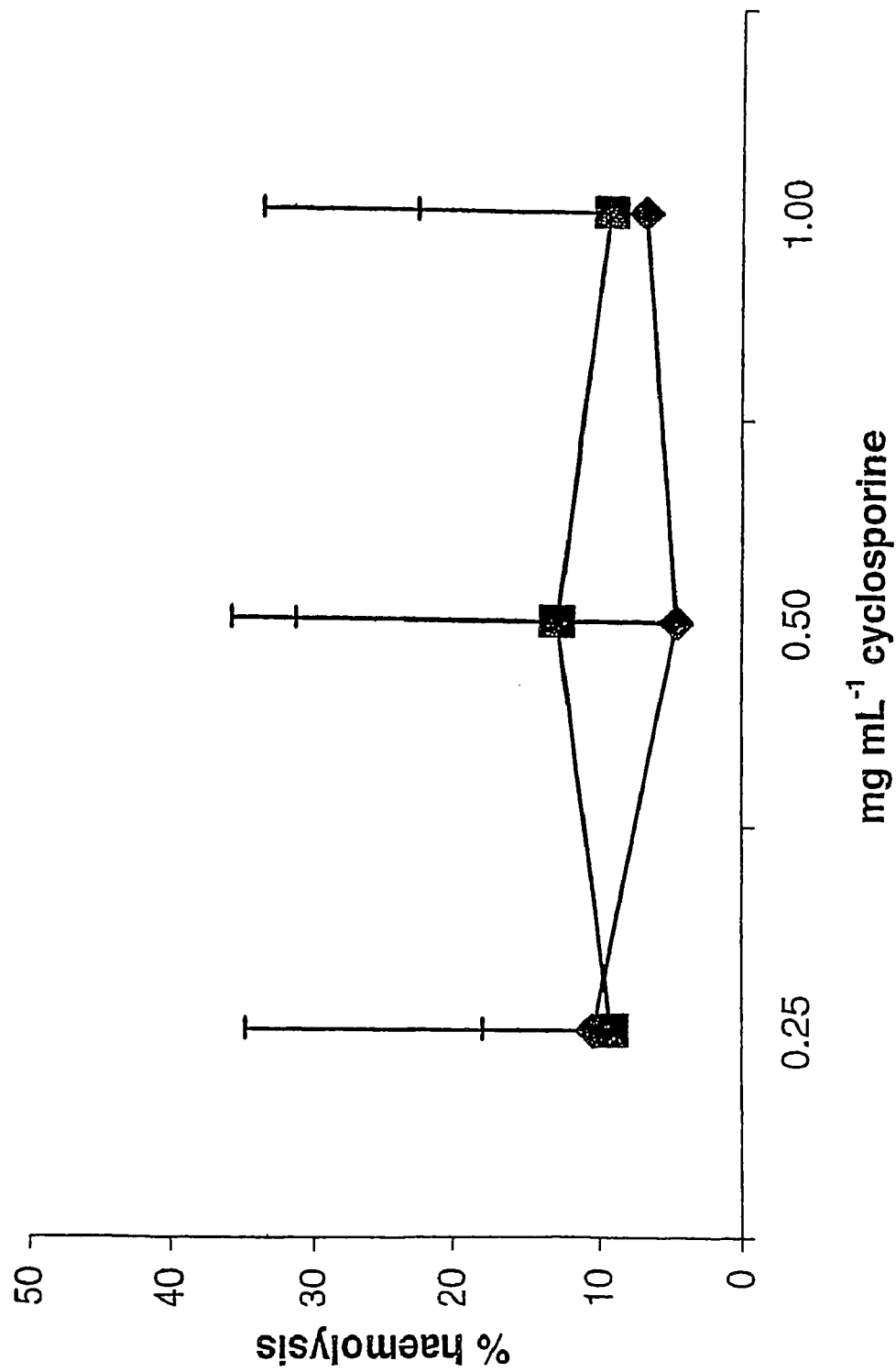
FIG. 2b is a representation of the haemolytic activity of GCPQ488 and cyclosporine in a 1:1 ratio.
Figure 2C:
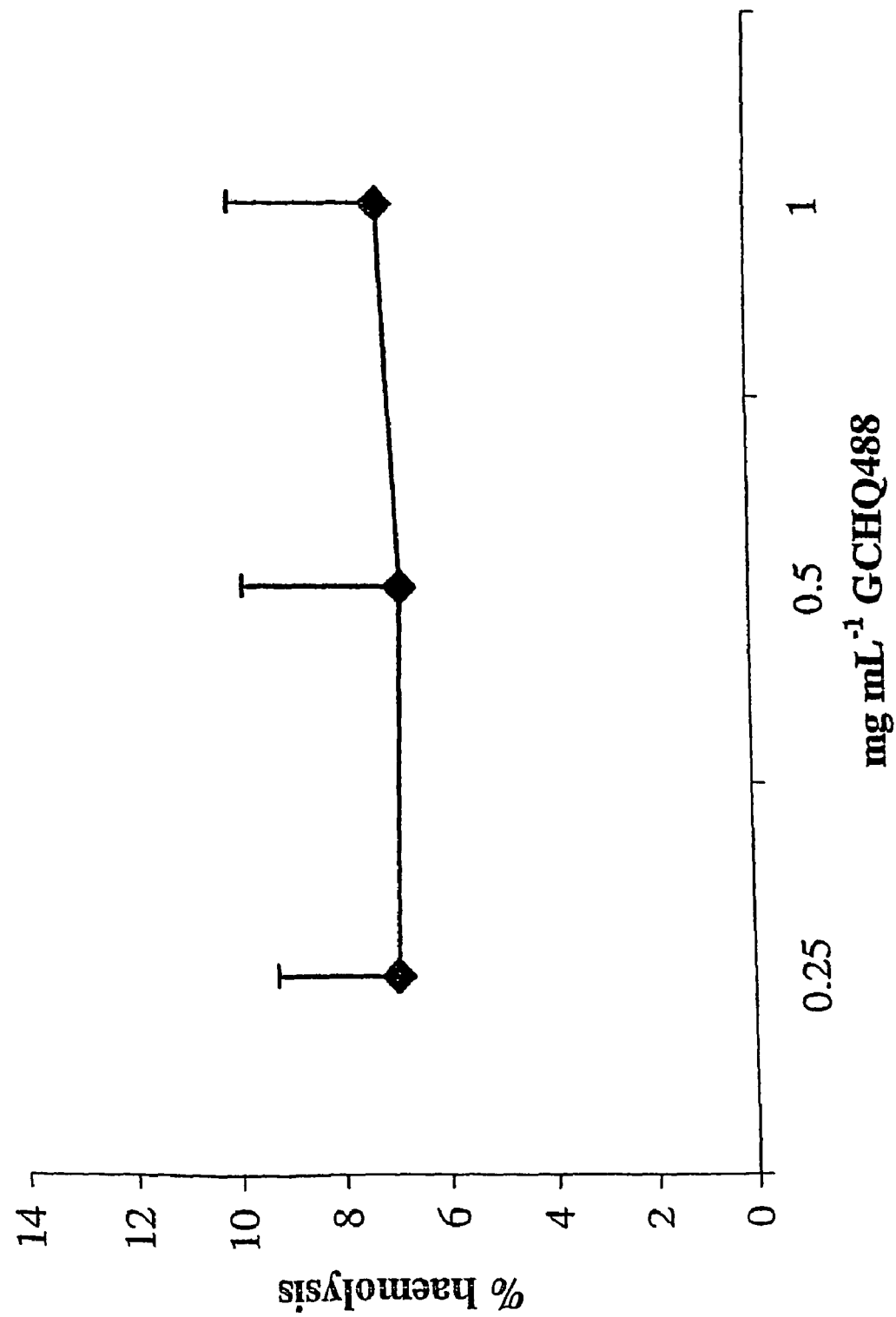
FIG. 2c is a representation of the haemolytic activity of GCHQ prepared from glycol chitosan which has been subjected to an initial 48 hours acid degradation and a further 8 hours degradation, followed by alkylation with hexadecyl bromide and alkylation with methyl iodide (i.e. GCHQ488)
Figure 2D:
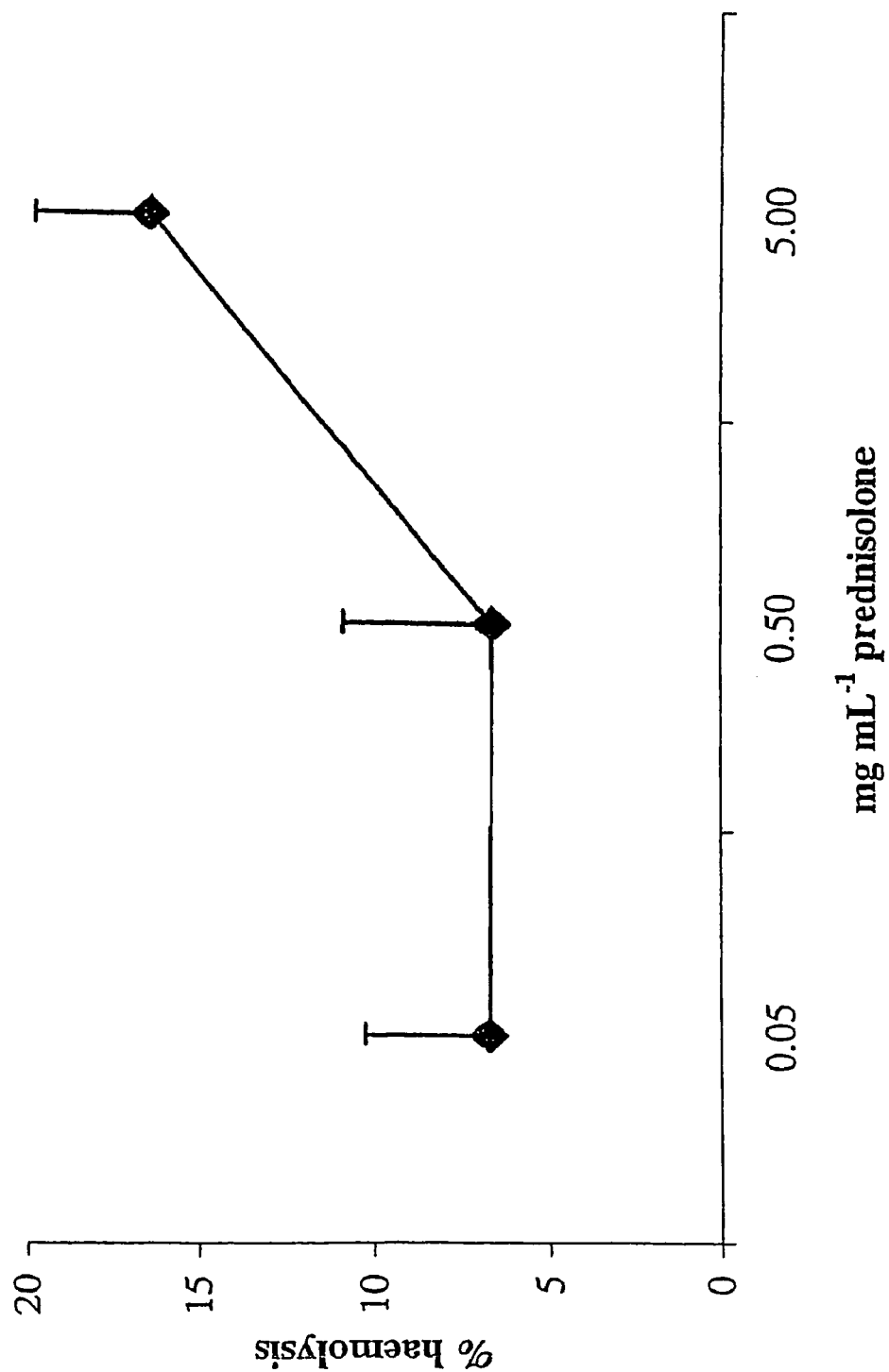
FIG. 2d is a representation of the haemolytic activity of GCHQ488 and prednisolone in a 1:5 ratio.
Figure 3A:
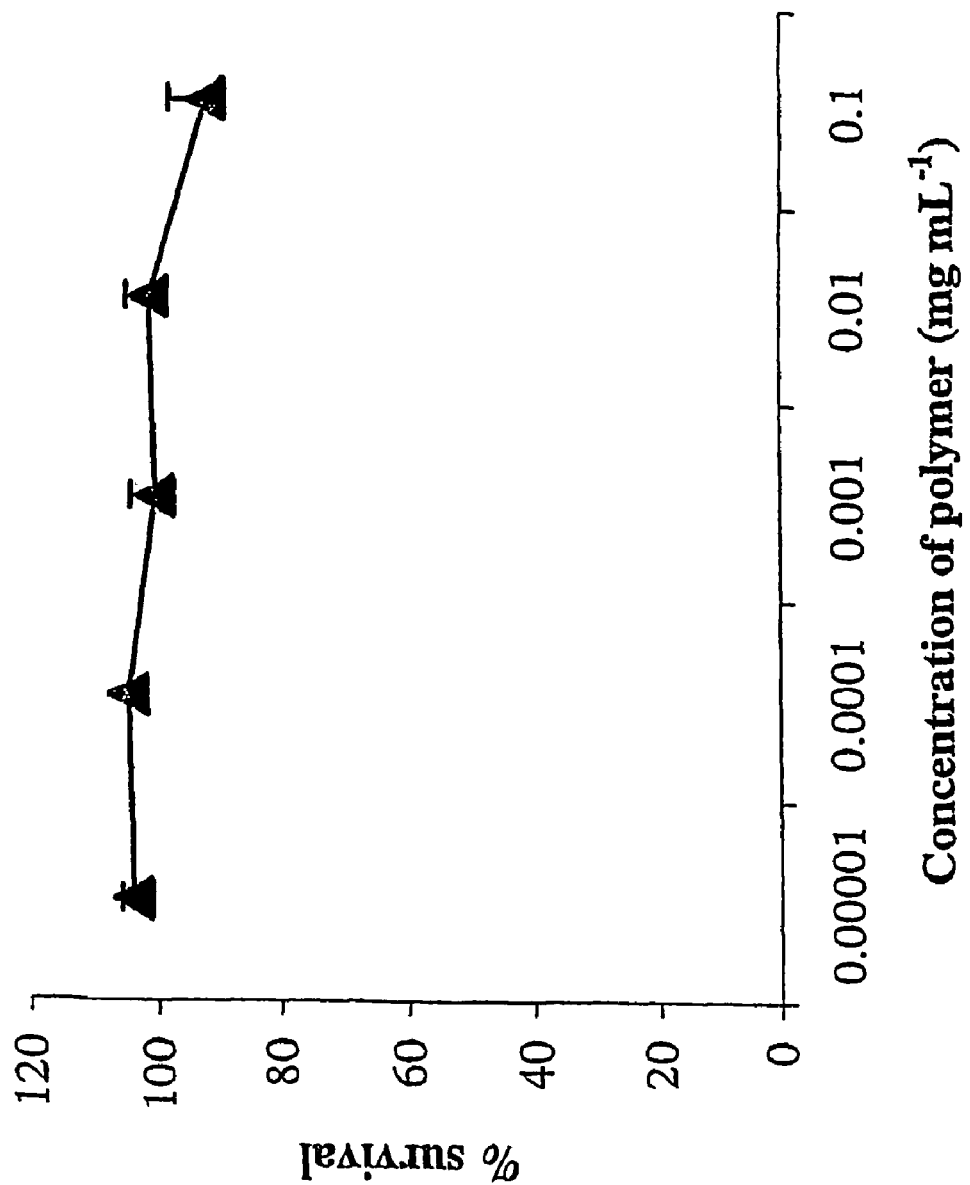
FIG. 3a is a representation of the cyctotoxicity to A549 cell lines after incubation with GCPQ488.
Figure 3B:
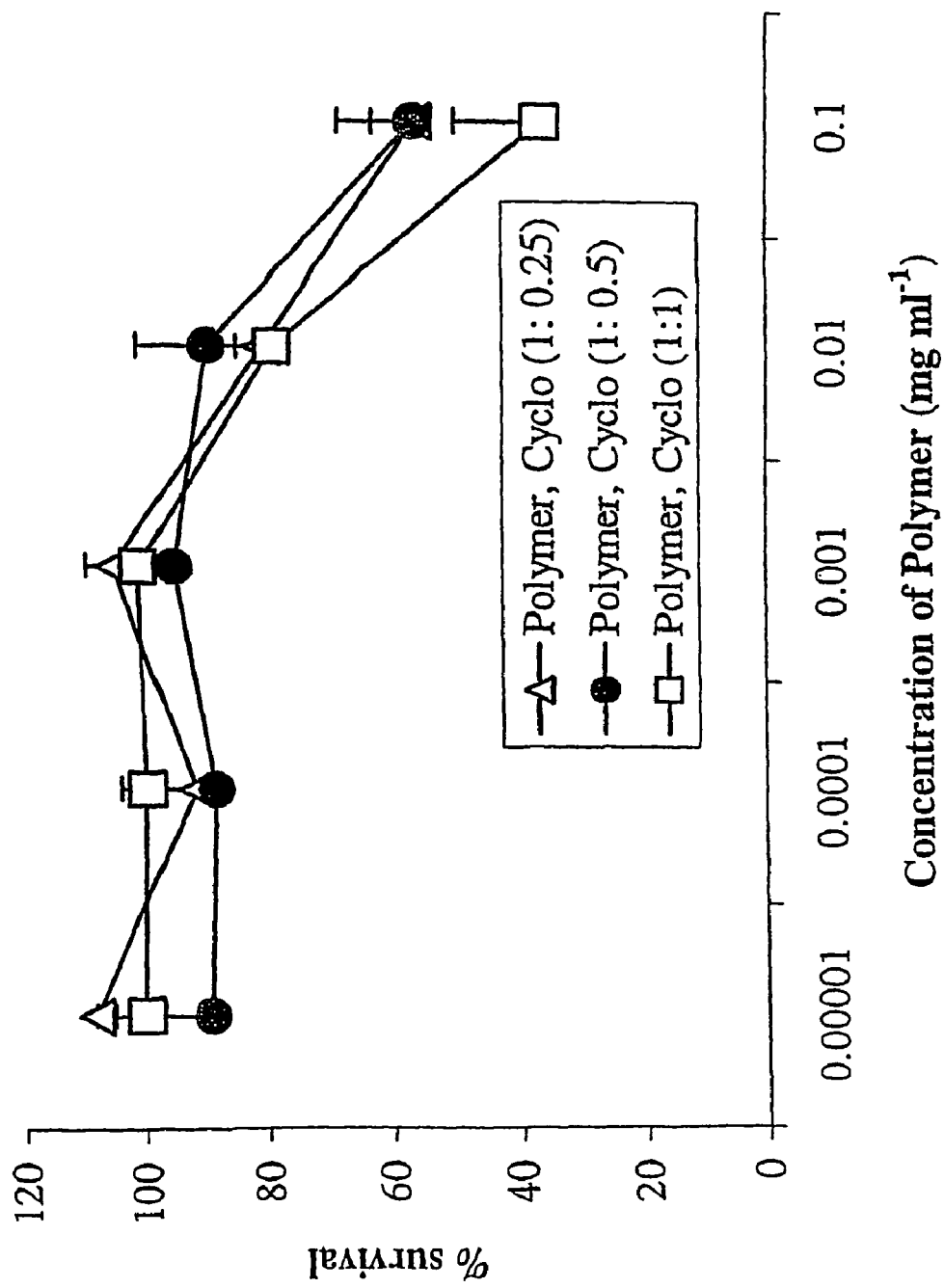
FIG. 3b is a representation of the cyctotoxicity to A549 cell lines after incubation with GCPQ488 and cyclosporine.
Figure 3C:
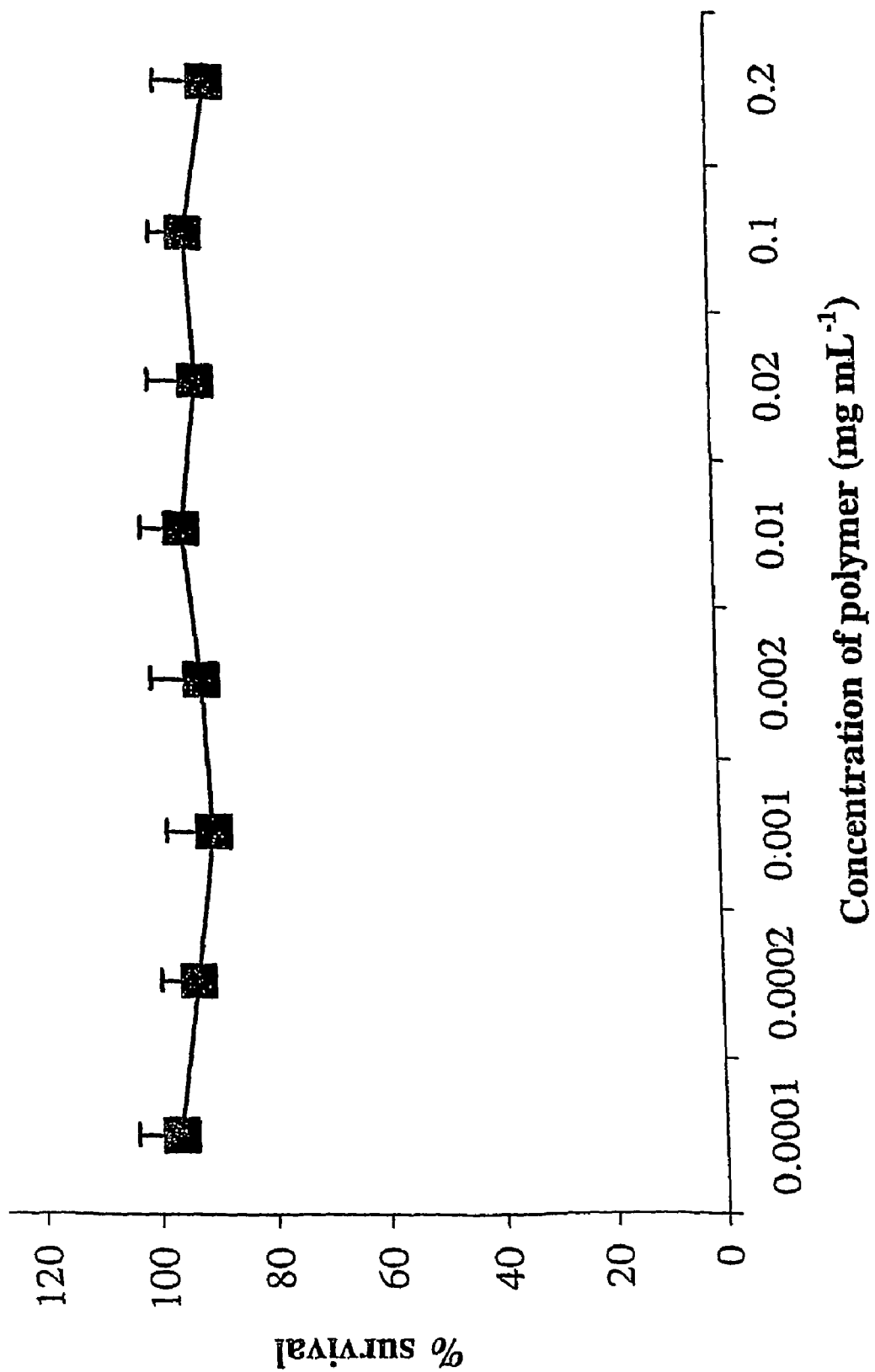
FIG. 3c is a representation of the cyctotoxicity to A549 cell lines after incubation with GCHQ488.
Figure 3D:
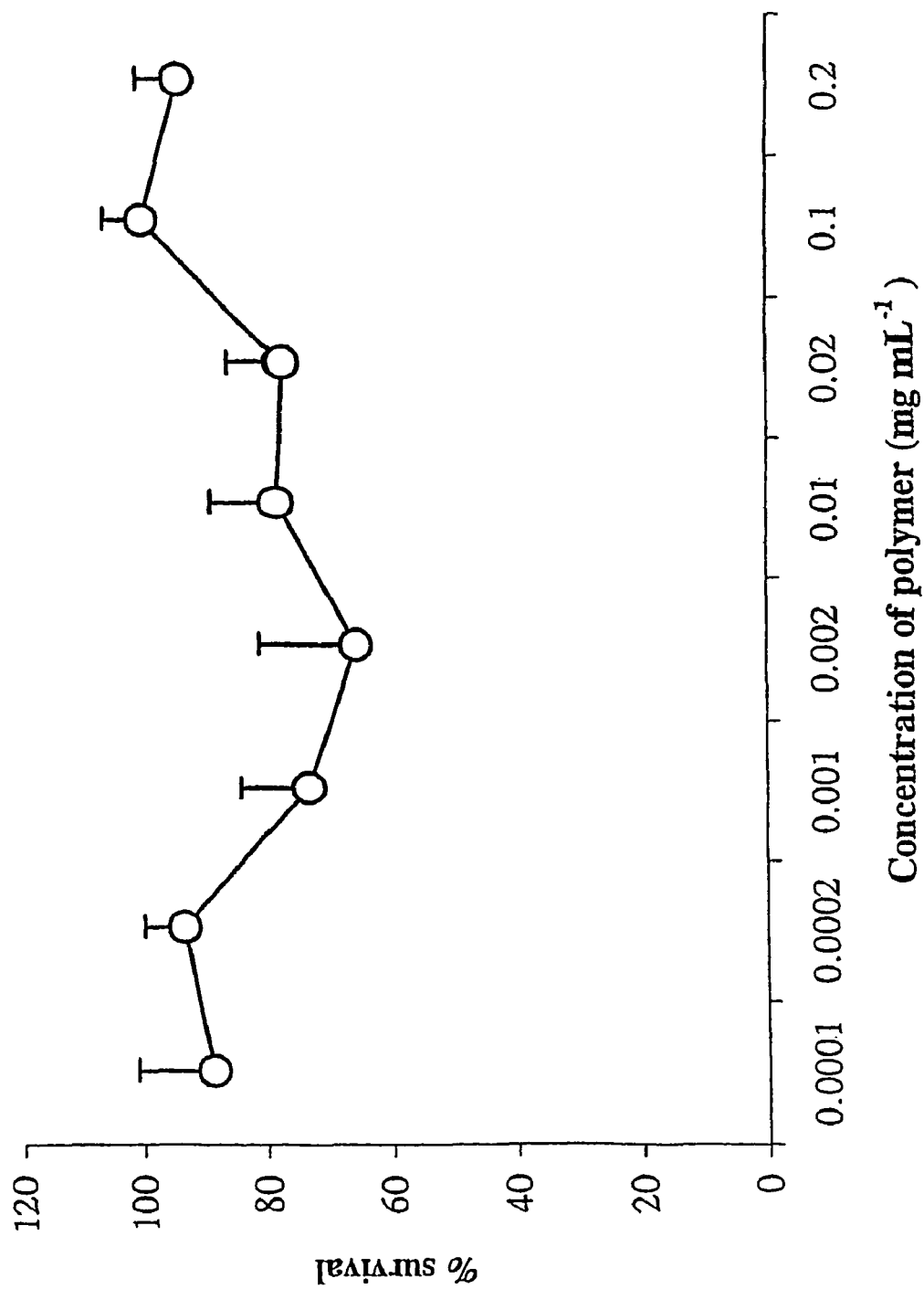
FIG. 3d is a representation of the cytotoxicity to A549 cell lines after incubation with GCHQ488 and prednisolone in a 1:5 ratio.
Figure 3E:
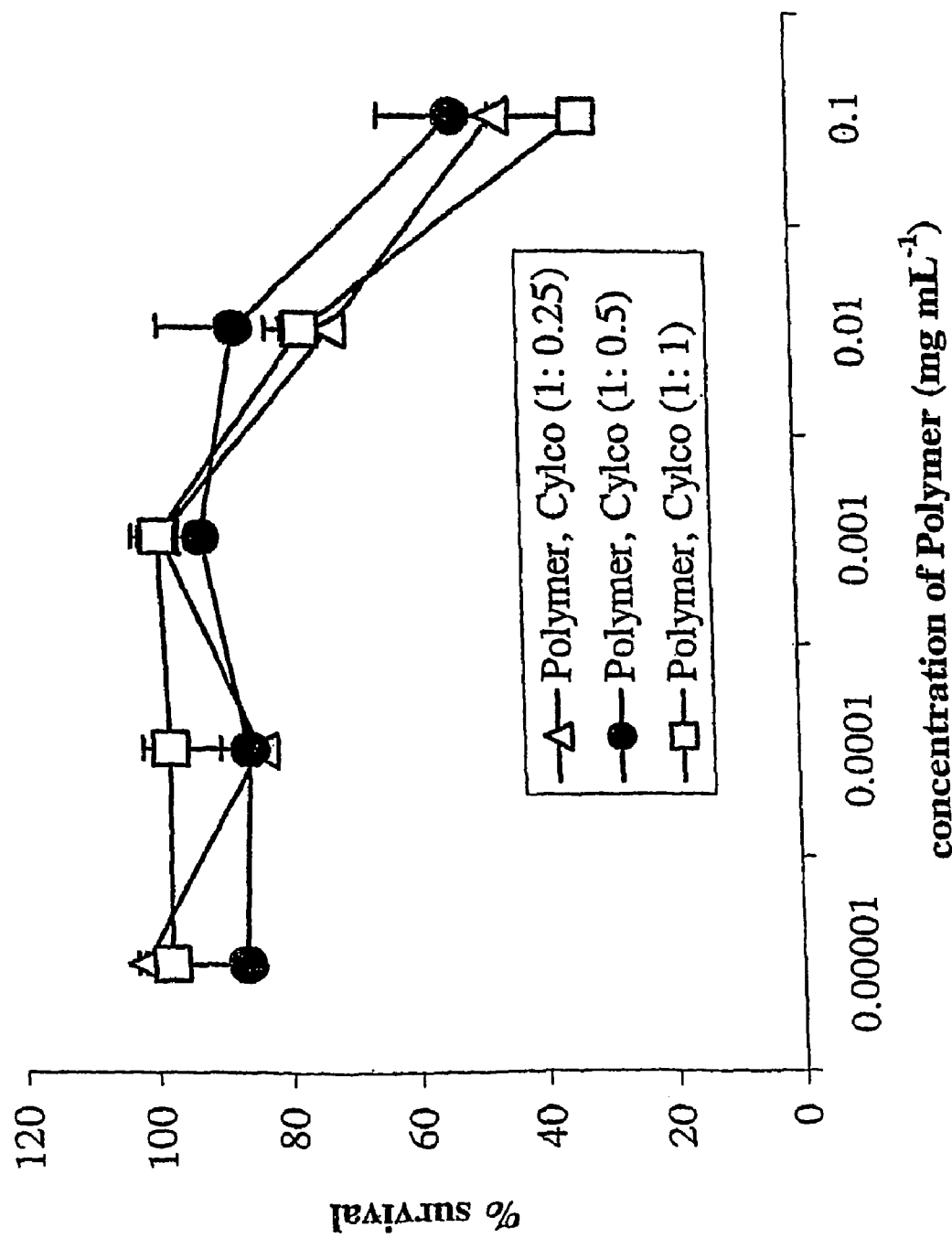
FIG. 3e is a representation of the cyctotoxicity to A431 cell lines after incubation with GCPQ488 and cyclosporine.
Figure 3F:
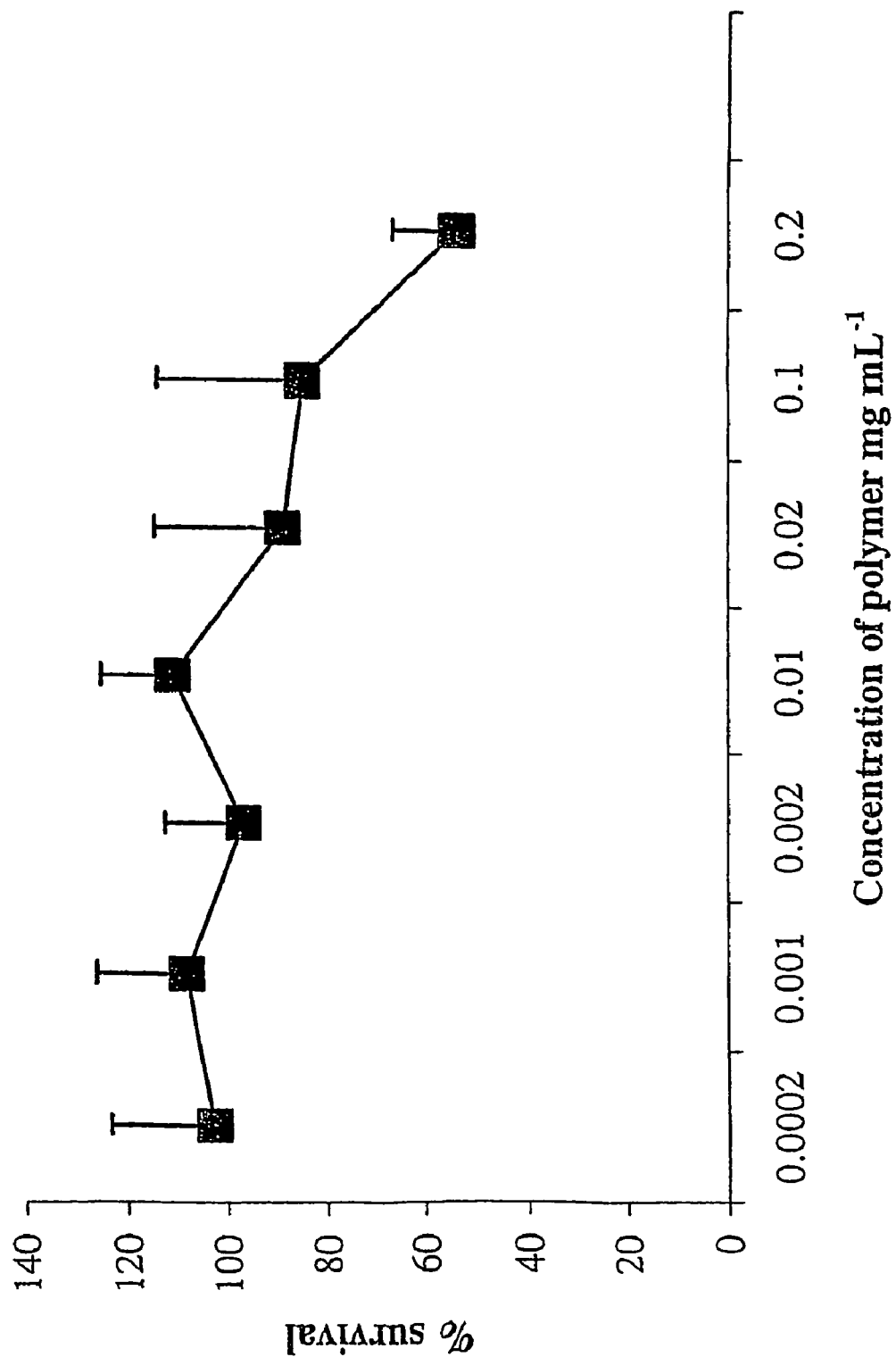
FIG. 3f is a representation of the cyctotoxicity to A431 cell lines after incubation with GCHQ488.
Figure 3G:
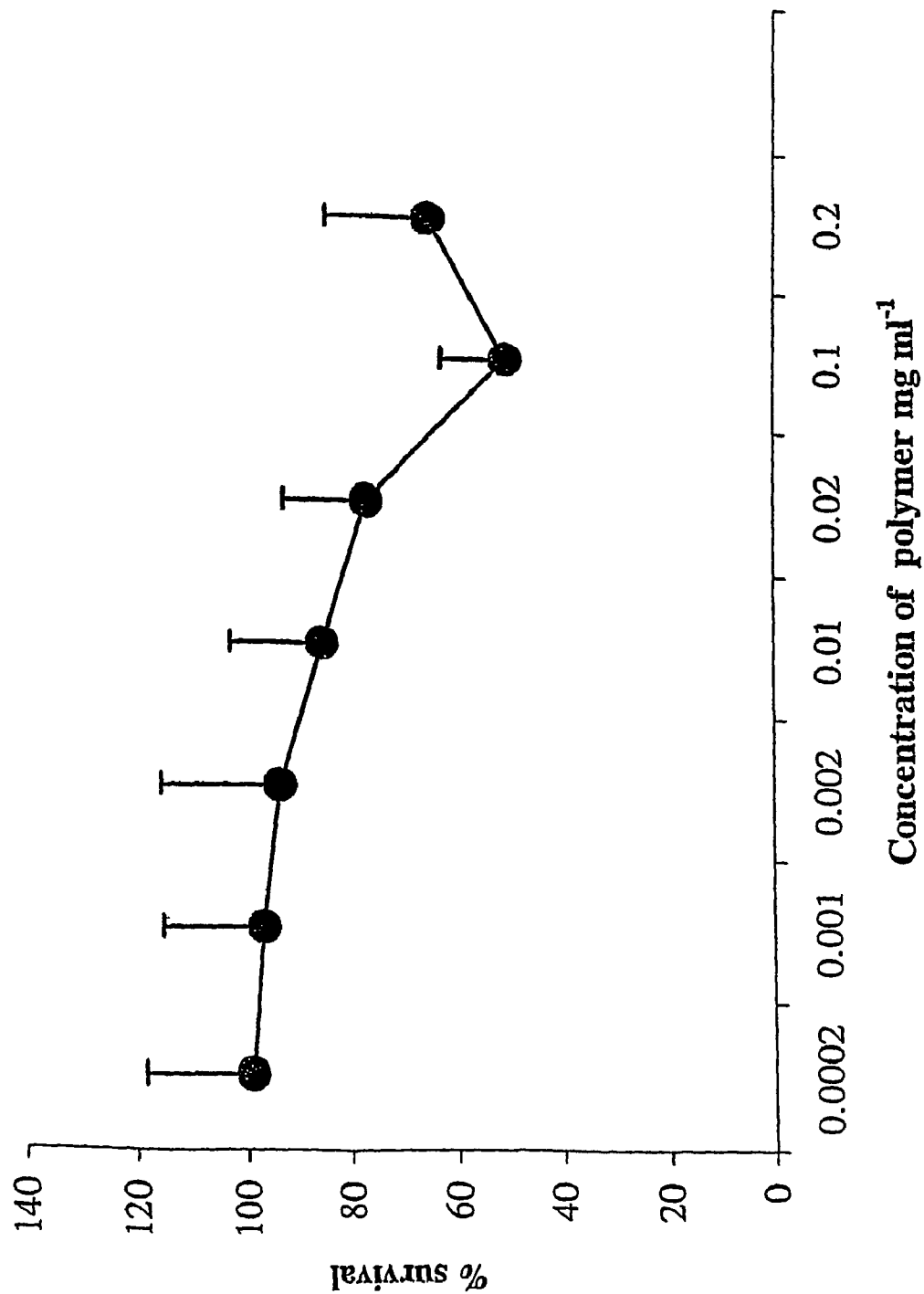
FIG. 3g is a representation of the cyctotoxicity to A431 cell lines after incubation with GCHQ488 and prednisolone in a 1:5 ratio.

The structures of GCPQ and GCHQ are shown in FIGS. 1a and 1b, respectively. GCPQ and GCHQ were recovered as white fibrous solids. With the glycol chitosan starting material as has been reported previously[15], an increase in the acid degradation time led to an increase in the degree of depolymerisation (Table 1), however after the initial 48 h there is a slowing down in the level of depolymerisation (Table 1).

TABLE 1

Molecular Weights of Glycol Chitosan Samples

| POLYMER | Acid Degradation Time | Molecular Weight (kD) | Polydispersity Mw/Mn |
|---|---|---|---|
| GC0 | 0 h | 104 | 1.05 |
| GC48 | 48 h | 19.3 | 1.20 |
| GC484 | 48 h + 4 h | 17.9 | 1.23 |
| GC488 | 48 h + 8 h | 17.2 | 1.28 |
| GC4824 | 48 h + 24 h | — | — |
| GC4848 | 48 h + 48 h | 15.2 | 1.08 |

The lipidic and quaternary ammonium derivatives of these glycol chitosan polymers are able to solubilise hydrophobic drugs such as prednisolone and cyclosporine in aqueous media as shown in Table 2.

TABLE 2

Solubilisation by Glycol Chiosan Polysoaps*

| Sample Name | GC Acid Degradation Time (h) | Molecular Weight (kD) of Glycol Chitosan starting material | Number of Palmitoyl or Hexadecyl* Groups per 100 sugar monomers (mole % hydrophobisation) | Number of Quaternary Ammonium Groups per 100 sugar Monomers (mole % Quaternisation) | Hyrophilicity Index (HI) = Mole % quaternisation/ Mole % palmitoylation OR Mole % Quaternisation/ Mole % Cetylation | Maxixmum Level of Prednisolone Solubilised (mg $mL^{-1}$) | Maximum Level of Cyclosporin Solubilised (mg $mL^{-1}$) |
|---|---|---|---|---|---|---|---|
| GCPQ484 | 4 | 17.9 | 7.7 | 11.3 | 1.47 | Polymer did not dissolve | polymer did not dissolve |
| GCPQ488 | 8 | 17.2 | 3.0 | 10.0 | 3.33 | 0.8 | 1.0 |
| GCPQ4824 | 24 | — | 3.6 | 16.0 | 4.44 | 1.0 | 1.0 |
| GCPQ4848 | 48 | 15.2 | 8.2 | 13.0 | 1.59 | 1.0 | 0.5 |
| GCHQ484 | 4 | 17.9 | 3.0* | 7.9 | 2.63 | Polymer did not dissolve | Polymer did not dissolve |
| GCHQ488 | 8 | 17.2 | 4.5* | 19.0 | 4.22 | 5 | 1 |
| CCHQ4824 | 24 | — | — | — | — | 0.5 | 0.5 |

*All polymers were present at a level of 1 mg $mL^{-1}$

All solutions were clear transparent liquids with optical density readings of less than 0.001 against distilled water which had an optical density of 0.000.

Solutions remained optically clear on dilution ten times with water. These solutions are in contrast to the chitosan—paclitaxel colloids reported by Miwa and others[11] where liquids with "turbidity" were obtained and the hydrophobic drug was added to the polymer formulation in the presence of 10% v/v of ethanol, with the removal of ethanol being attempted but not confirmed.

$^1$H NMR was used to quantify the level of quaternisation, acylation and alkylation and a value for the hydrophilicity index (HI) is quoted in Table 2. The HI (derived from the $^1$H NMR data) is a term used here to characterise the hydrophilicity of the polymers and this value quantifies the relationship between additional ionic hydrophilic substituents and hydrophobic substituents added to a previously aqueous soluble polymer or aqueous soluble polymer derivative. Aqueous soluble polymers are described as polymers soluble in water at a level of above 1 mg mL$^{-18}$. These carbohydrate polymers may be additionally substituted with non-ionic hydrophilic units as is shown here.

The data in Table 3 shown below, shows that the polymers aggregate in aqueous media to produce hydrophobic domains as evidenced by the increase in the $I_3/I_1$ ratio.

TABLE 3

I3/I1 data for GCPQ and GCHQ Polymers

| Polymer Concentration | I3/I1 | | | | |
|---|---|---|---|---|---|
| | GCPQ488B | GCPQ4824B | GCPQ4848B | GCHQ488B | GCHQ4824B |
| 0 | 0.67 | 0.67 | 0.67 | 0.67 | 0.67 |
| 0.25 | — | — | 0.91 | — | — |
| 0.5 | 0.67 | 0.82 | 0.88 | 0.80 | 0.85 |
| 1 | 0.97 | 0.85 | 1.02 | 0.86 | 1.02 |
| 1.5 | 1.02 | — | — | 0.91 | 1.18 |
| 2.0 | 1.28 | 0.86 | 0.92 | 1 | 1.25 |

[B merely means a different batch of polymer]

These hydrophobic domains provide areas for the solubilisation of hydrophobic solutes while the hydrophilic substituents increase the affinity of the polymer with the aqueous solvent and prevent phase separation.

As shown in Table 3 the hydrophobicity of the polymer aggregates when present at a polymer concentration of 1 mg mL$^{-1}$ (as determined using a pyrene probe) followed the trend GCHQ4824=GCPQ4848>GCPQ488>GCHQ488=GCPQ4824. This hydrophobicity ranking obtained by the use of the pyrene probe is similar to the hydrophobicity ranking obtained using the HI: GCPQ4848=1.58, GCPQ488=3.33, GCHQ488#1 (i.e. different batch of polymer)=4.22 and GCPQ4824=4.44. (Table 2). Additionally the maximum level of drug solubilised in the case of the more polar drug prednisolone is solubilised by GCHQ488 (Tables 2&4), one of the more polar polysoaps (Table 2).

TABLE 4

Prednisolone Stability Studies

| Polymer | Polymer Concentration (mg mL$^{-1}$) | Age of Formulation | Storage Conditions | Original Prednisolone Concentrations (mg mL$^{-1}$) | Prednisolone Detected (mg mL$^{-1}$) |
|---|---|---|---|---|---|
| GCPQ488 | 1 | 15 weeks | RT | 1.0 | 0.2 |
| GCPQ488 | 1 | 15 weeks | 4° C. | 0.75 | 0.2 |
| GCHQ488 | 1 | 12 weeks | RT | 5.0 | 4.5 |
| GCHQ488A* | 1 | 2 weeks | 4° C. | 2.5 | 2.4 |
| GCHQ488A* | 1 | 10 weeks | 4° C. | 2.5 | 2.4 |
| GCHQ488A* | 1 | 2 weeks | 4° C. | 5.0 | 4.4 |
| GCHQ488A* | 1 | 10 weeks | 4° C. | 5.0 | 4.3 |

*= different batch of GCHQ488

TABLE 5

Cyclosporine Stability Studies

| Lymer | Polymer Concentrations | Age of formulation | Storage Conditions | Initial Level of Cyclosporine (mg mL$^{-1}$) | Cyclosporine Detected (mg mL$^{-1}$) |
|---|---|---|---|---|---|
| GCPQ488 | 1 | 1 day | 4° C. | 1 | 0.95 |
| GCPQ488 | 1 | 3 days | 4° C. | 1 | 0.92 |
| GCPQ488 | 1 | 1 week | 4° C. | 1 | 1.10 |
| GCPQ488 | 1 | 2 weeks | 4° C. | 1 | 1.10 |
| GCPQ488 | 1 | 4 weeks | 4° C. | 1 | 0.90 |
| GCPQ488 | 1 | 8 weeks | 4° C. | 1 | 0.80 |
| GCPQ488 | 1 | 12 weeks | 4° C. | 1 | 0.70 |
| GCPQ488 | 1 | 15 weeks | 4° C. | 1 | 0.80 |
| GCPQ488 | 1 | 22 weeks | 4° C. | 1 | 0.70 |

Also the least polar polysoaps (with the lowest HI value) and the highest molecular weight i.e.—GCPQ484 and GCHQ484 are insoluble in water at a level of 1 mg mL$^{-1}$ (Tables 1 and 2).

Relatively high levels of hydrophobicity also hamper (albeit to a lesser extent) the solubilisation of cyclosporine, as evidenced by the rather low maximum levels of cyclosporine solubilised by GCPQ4848 and GCHQ4824. This is shown in Table 5 below.

TABLE 5-continued

Cyclosporine Stability Studies

| Lymer | Polymer Concentrations | Age of formulation | Storage Conditions | Initial Level of Cyclosporine (mg mL$^{-1}$) | Cyclosporine Detected (mg mL$^{-1}$) |
|---|---|---|---|---|---|

The solubilising polymer must thus be depolymerised as well as substituted with a controlled number of hydrophobic and hydrophilic moieties. Within the molecular weight range (10-20 kD), HI (when calculated from the $^1$H NMR) values of above about 2 appear to be the most efficient polymers in the case of the more polar palmitoyl substituent and HI values above about 3 appear to be the most efficient solubilisers in the case of the less polar hexadecyl substituents (Table 2). Clearly in the case of prednisolone and cyclosporine, a high level of quaternisation and low level of hydrophobic modification favours solubilisation with these polymers (Tables 1-4).

With the N-lauroyl 6-carboxymethyl chitosan polymers prepared previously[11], a shift to a higher level of the carboxymethyl groups and a lower level of lauroyl groups resulted in a decreased association of paclitaxel with the chitosan based colloid. In the present invention, the ability of the polymer molecule to be fully hydrated by water molecules (presence of ionic quaternary ammonium groups) plays a more important role than the ability of the polymer to aggregate into polymeric micelles (presence of hydrophobic groups) and provide a hydrophobic cavity within which hydrophobic solutes may be shielded.

The solubilising polymer should be prepared from an aqueous soluble and depolymerised carbohydrate and the most effective polymers have a degree of polymerisation of less than 200 monomer units. The solubilising polymer may further have a level of hydrophobic substitution not exceeding 10 substituents per every 100 monomers and finally an additional ionic hydrophilic substitution level of equal to or more than 1 substituent per polymer chain. There may be an optional additional hydrophilic substituent of at least 1 hydrophilic substituent per polymer chain. Previous work with N-lauroyl 6-carboxymethyl chitosan has shown that there is no increase in the association of paclitaxel with the chitosan based colloid on reducing the degree of polymerisation from a molecular weight of 50 kD to 2 kD[11]. However, it is shown herewith that even small changes in molecular weight affect the solubilising properties of the polymers as evidenced by the data presented on GCPQ484 and GCPQ4848 (Table 2).

Finally, in the work described using N-lauroyl 6-carboxymethylchitosan, polymers encapsulating paclitaxel had a level of hydrophobic substitution exceeding 20 substituents per 100 monomers and a minimum level of 140 carboxymethyl groups per 100 monomers[11]. In contrast the present invention relates to a maximum level of 10 hydrophobic substituents per 100 monomer units.

The solubilising polymer of the present invention may contain additional targeting groups such as peptides, antibodies and other ligands e.g. folate and transferrin ligands which will allow the polymer to target endogenous receptors and thus target its drug payload to such endogenous receptors at the site of pathology.

With the HPLC assays used the retention time of prednisolone was 2.7 min and the standard curve had a correlation coefficient of 0.998 while the retention time for cyclosporine was 13.7 min and the standard curve had a correlation coefficient of 0.98. Solubilised material was stable for up to 12 weeks with chitosan based polymer formulations retaining up to 9.0% of solubilised drug for this length of time (Tables 4 and 5).

The solubilising polymers presented herein are biocompatible. Solutions of the GCPQ488 and GCPQ488, cyclosporine samples in water resulted in a maximum 40% cell lysis, while formulations within isotonic PBS (pH=7.4) gave about 10% cell lysis up to a polymer concentration of 1 mg mL$^{-1}$ (FIG. 2). The hypotonic water environment is thus responsible for the observed cell lysis. While the inclusion of up to 1 mg mL$^{-1}$ cyclosporine within polymer formulations appeared to protect the cells from lysis (especially in the presence of water as the solvent), the inclusion of 5 mg mL$^{-3}$ prednisolone increased the level of lysis observed with the polymers (FIG. 2). It is concluded that these glycol chitosan polysoaps show no appreciable levels of haemolysis to cells. However, what should be noted here is the observation of drug activity in the presence of the polysoaps.

Below a level of 0.1 mg mL$^{-1}$ none of the glycol chitosan based polysoaps are particularly cytotoxic in both the A431 and the A549 cell lines (FIG. 3). However the addition of either prednisolone or cyclosporine does cause the appearance of some cytotoxicity although none of the formulations resulted in the observation of less than 50% cell survival below a polymer concentration of 0.01 mg mL$^{-1}$. It may be concluded that the glycol chitosan polysoaps are not particularly cytotoxic polymers and any toxicity seen with the drug formulations is largely due to the addition of drug and not due to the toxicity of the polymer per se. Once again what should be noted here is the observation of drug activity in the presence of the polysoaps.

Example 2

This Example relates to a high throughput method of selection of carbohydrate solubilisers Materials Glycol chitosan, palmitic acid N-hydroxysuccinimide, methyl iodide, N-methyl pyrrolidone, sodium iodide, sodium hydroxide, prednisolone and 6-methyl prednisolone were all obtained from Sigma-Aldrich Co. UK. Absolute ethanol was supplied by Bamford Laboratories, UK and diethyl ether by BDH Laboratories, UK. Acetonitrile was supplied by Riedel de-Haen, Germany.

Methods

Degradation of Glycol Chitosan (GC)

Glycol chitosan (GC) was degraded for 48 h as described above[15]. 25 quaternary ammonium palmitoyl glycol chitosan polymers were synthesised from the degraded material with differing levels of hydrophobic (palmitoyl) and hydrophilic (quaternary ammonium) substitution.

Solutions of palmitic acid N-hydroxysuccinimide (PNS) in ethanol (5.28 mg mL$^{-1}$), sodium iodide (2 mg mL$^{-1}$) in N-methyl pyrrolidone (NMP), sodium hydroxide in absolute ethanol (10 mg mL$^{-1}$), glycol chitosan (10 mg mL$^{-1}$, GC) in a solution of sodium bicarbonate (7.53 mg mL$^{-1}$) and prednisolone (10 mg mL$^{-1}$) in methanol were prepared.

25 different polymers were synthesised by adding a solution of palmitic acid N-hydroxysuccinimide at the levels shown in Table 1 to the glycol chitosan—sodium bicarbonate solution (1 mL) contained in a 25 mL test tube. The tubes were shaken for 16 h at room temperature and subsequently heated at 85° C. for 4 h to evaporate off the ethanol.

The residues in the tubes were extracted with diethyl ether (3×15 mL) to remove unreacted palmitic acid and subsequently washed with absolute ethanol to remove polar contaminants. Ethanol was removed and residual ethanol was dried under a stream of nitrogen. For the quaternisation reaction the solution of sodium iodide in NMP was added to the test tubes in the quantities shown in Table 1. This was followed by the addition of the solution of sodium hydroxide and the addition of methyl iodide in the quantities shown in Table 1.

The tubes were heated for 3 h at 36° C. and diethyl ether added to the tubes (5 mL). This caused the quaternary ammonium product to precipitate. The supernatant was decanted from the tubes and the residues washed with diethyl ether (3×5mL). The residue was then left to dry overnight and water (2 mL) subsequently added to each tube to produce polymer solutions known herein as "concentrated polymer solutions". To a separate set of 25 tubes was added 0.1 mL of the prednisolone solution in methanol. Methanol was removed under a stream of nitrogen and to each tube was added a sample of one of the 25 quaternary ammonium palmitoyl glycol chitosan solutions (1 mL) from above.

This mixture was probe sonicated (MSE Instruments, Sanyo, UK) filtered using a 0.45 μm filter and analysed by high performance liquid chromatography (HPLC). The polymer solutions obtained from the synthesis step above were diluted by adding to 1 mL each of the 25 solutions to an additional volume of water (1 mL) to produce what are termed here as "dilute polymer solutions" and the prednisolone solubilisation procedure described above repeated once more with a more dilute solution of the synthesised polymer.

Prednisolone levels were analysed in filtered (0.45 μm) samples of the polymer—drug formulation by HPLC. Samples (20 μL), appropriately diluted with the mobile phase (acetonitrile, water 36:64) and containing 6-methyl prednisolone (1 μg mL$^{-1}$) were injected onto a reverse phase Symmetry C18, 3.5 μm column (4.6 mm×75 mm, Waters Instruments, UK) by means of a Waters 717 autosampler and a Waters 515 isocratic pump. Peak detection was via a Waters 486 variable wavelength UV detector with the wavelength set at 243 nm and data was collected using Waters Empower software. The mobile phase was set at a flow rate of 1 ml min$^{-1}$. A standard curve was prepared with 6-methyl prednisolone (1 μg mL–1) as the internal standard and with samples of prednisolone solubilised in the mobile phase (0.1-20 μg mL$^{-1}$)

TABLE 6

High throughput polymer synthesis–reagent volumes (mL)

| Increasing methyl iodide (hydrophilic substitution) | Increasing palmitic acid N-hydroxysuccinimide (hydrophobic substitution) | | | | |
|---|---|---|---|---|---|
| | Polymer E1 | Polymer E2 | Polymer E3 | Polymer E4 | Polymer E5 |
| | PNS - 0.5 | PNS - 1 | PNS - 2 | PNS - 3 | PNS - 4 |
| | NaI - 3.0 | NaI - 3.0 | NaI - 3.0 | NaI - 3.0 | NaI - 3.0 |
| | NaOH - 0.6 | NaOH - 0.6 | NaOH - 0.6 | NaOH - 0.6 | NaOH - 0.6 |
| | CH$_3$I - 0.062 | CH$_3$I - 0.062 | CH$_3$I - 0.062 | CH$_3$I - 0.062 | CH$_3$I - 0.062 |
| | Polymer D1 | Polymer D2 | Polymer D3 | Polymer D4 | Polymer D5 |
| | PNS - 0.5 | PNS - 1 | PNS - 2 | PNS - 3 | PNS - 4 |
| | NaI - 2.5 | NaI - 2.5 | NaI - 2.5 | NaI - 2.5 | NaI - 2.5 |
| | NaOH - 0.5 | NaOH - 0.5 | NaOH - 0.5 | NaOH - 0.5 | NaOH - 0.5 |
| | CH$_3$I - 0.052 | CH$_3$I - 0.052 | CH$_3$I - 0.052 | CH$_3$I - 0.052 | CH$_3$I - 0.052 |
| | Polymer C1 | Polymer C2 | Polymer C3 | Polymer C4 | Polymer C5 |
| | PNS - 0.5 | PNS - 1 | PNS - 2 | PNS - 3 | PNS - 4 |
| | NaI - 2 | NaI - 2 | NaI - 2 | NaI - 2 | NaI - 2 |
| | NaOH - 0.4 | NaOH - 0.4 | NaOH - 0.4 | NaOH - 0.4 | NaOH - 0.4 |
| | CH$_3$I - 0.042 | CH$_3$I - 0.042 | CH$_3$I - 0.042 | CH$_3$I - 0.042 | CH$_3$I - 0.042 |
| | Polymer B1 | Polymer B2 | Polymer B3 | Polymer B4 | Polymer B5 |
| | PNS - 0.5 | PNS - 1 | PNS - 2 | PNS - 3 | PNS - 4 |
| | NaI - 1.5 | NaI - 1.5 | NaI - 1.5 | NaI - 1.5 | NaI - 1.5 |
| | NaOH - 0.3 | NaOH - 0.3 | NaOH - 0.3 | NaOH - 0.3 | NaOH - 0.3 |
| | CH$_3$I - 0.032 | CH$_3$I - 0.032 | CH$_3$I - 0.032 | CH$_3$I - 0.032 | CH$_3$I - 0.032 |
| | Polymer A1 | Polymer A2 | Polymer A3 | Polymer A4 | Polymer A5 |
| | PNS - 0.5 | PNS - 1 | PNS - 2 | PNS - 3 | PNS - 4 |
| | NaI - 1 | NaI - 1 | NaI - 1 | NaI - 1 | NaI - 1 |
| | NaOH - 0.2 | NaOH - 0.2 | NaOH - 0.2 | NaOH - 0.2 | NaOH - 0.2 |
| | CH$_3$I - 0.022 | CH$_3$I - 0.022 | CH$_3$I - 0.022 | CH$_3$I - 0.022 | CH$_3$I - 0.022 |

All values are in ml.

Results

TABLE 7

High throughput polymer synthesis–prednisolone solubilities with concentrated polymer solutions (mg mL$^{-1}$)

| Increasing methyl iodide (hydrophilic substitution) | Increasing palmitic acid N-hydroxysuccinimide (hydrophobic substitution) | | | | |
|---|---|---|---|---|---|
| | Polymer E1 | Polymer E2 | Polymer E3 | Polymer E4 | Polymer E5 |
| | 0.472 | 0.613 | 0.632 | — | — |

TABLE 7-continued

High throughput polymer synthesis–prednisolone solubilities with concentrated polymer solutions (mg mL$^{-1}$)

| Increasing methyl iodide (hydrophilic substitution) | Increasing palmitic acid N-hydroxysuccinimide (hydrophobic substitution) | | | |
|---|---|---|---|---|
| Polymer D1 0.984 | Polymer D2 0.978 | Polymer D3 0.828 | Polymer D4 0.847 | Polymer D5 0.906 |
| Polymer C1 0.433 | Polymer C2 0.374 | Polymer C3 0.346 | Polymer C4 0.399 | Polymer C5 0.374 |
| Polymer B1 0.373 | Polymer B2 0.166 | Polymer B3 0.128 | Polymer B4 0.369 | Polymer B5 0.367 |
| Polymer A1 0.598 | Polymer A2 0.590 | Polymer A3 — | Polymer A4 — | Polymer A5 0.512 |

TABLE 8

High throughput polymer synthesis–prednisolone solubilities with dilute polymer solutions (mg mL$^{-1}$)

| Increasing methyl iodide (hydrophilic substitution) | Increasing palmitic acid N-hydroxysuccinimide (hydrophobic substitution) | | | |
|---|---|---|---|---|
| Polymer E1 0.987 | Polymer E2 0.830 | Polymer E3 — | Polymer E4 — | Polymer E5 — |
| Polymer D1 0.954 | Polymer D2 0.802 | Polymer D3 0.847 | Polymer D4 0.713 | Polymer D5 0.633 |
| Polymer C1 0.831 | Polymer C2 0.700 | Polymer C3 0.625 | Polymer C4 0.776 | Polymer C5 0.731 |
| Polymer B1 0.816 | Polymer B2 0.785 | Polymer B3 0.860 | Polymer B4 0.680 | Polymer B5 0.626 |
| Polymer A1 0.993 | Polymer A2 0.956 | Polymer A3 0.691 | Polymer A4 0.644 | Polymer A5 0.646 |

Comment on Results

The high through put method outlined above was able to select polymers with a high solubilising ability (e.g. Polymer E1) for a particular drug which in this case was prednisolone. Polymer E1 may then be synthesised in bulk quantities. Lower concentrations of the polymer (dilute polymer solutions) of about 0.01-5 m m$^{-1}$ were superior solubilisers of the model drug than higher concentrations (of about 5-10 mg mL$^{-1}$) of the polymer.

REFERENCES

1. Laschewsky, A., *Molecular concepts, self-organisation and properties of polysoaps*. Advances in Polymer Science, 1995. 124: p. 1-86.
2. Yang, Y. J. and J. Engberts, *Preparation and Stability of Polystyrene Latexes Using Polysoaps as Emulsifiers*. European Polymer Journal, 1992. 28: p. 881-886.
3. Anton, P. and A. Laschewsky, *Solubilization by Polysoaps*. Colloid and Polymer Science, 1994. 272: p. 1118-1128.
4. Yang, Y. J. and J. Engberts, *Fluorescence Spectroscopic Study of the Formation of Hydrophobic Microdomains in Aqueous-Solutions of Poly(Alkylmethyldiallylammonium Bromides)*. Recueil Des Travaux Chimiques Des Pays-Bas-Journal of the Royal Netherlands Chemical Society, 1991. 110: p. 384-386.
5. Cochin, D., F. Candau, R. Zana, and Y. Talmon, *Direct Imaging of Microstructures Formed in Aqueous-Solutions of Polyamphiphiles*. Macromolecules, 1992. 25: p. 4220-4223.
6. Binanalimbele, W. and R. Zana, *Fluorescence Probing of Microdomains in Aqueous-Solutions of Polysoaps 0.2. Study of the Size of the Microdomains*. Macromolecules, 1990. 23: p. 2731-2739.
7. Florence, A. T. and D. Attwood, *Physicochemical Principles of Pharmacy*. 1998, Basingstoke: Macmillan Press.
8. Medicines, Commission, *British Pharmacopoeia*. 1998, London: The Stationery Office.
9. Yoshioka, H., K. Nonaka, K. Fukuda, and S. Kazama, *Chitosan-Derived Polymer-Surfactants and Their Micellar Properties*. Bioscience Biotechnology and Biochemistry, 1995. 59: p. 1901-1904.
10. Gautier, S., M. Boustta, and P. Vert, *Alkylated poly(L-lysine citramide) as models to investigate the ability of amphiphilic macromolecular drug carriers to physically entrap lipophilic compounds in aqueous media*. Journal of Controlled Release, 1999. 60: p. 235-247.
11. Miwa, A., A. Ishibe, M. Nakano, T. Yamahira, S. Itai, S. Jinno, and H. Kawahara, *Development of novel chitosan derivatives as micellar carriers of taxol*. Pharmaceutical Research, 1998. 15: p. 1844-1850.
12. Kjoniksen, A. L., B. Nystrom, C. Iversen, T. Nakken, O. Palmgren, and T. Tande, *Viscosity of dilute aqueous solutions of hydrophobically modified chitosan and its unmodified analogue at different concentrations of salt and surfactant concentrations*. Langmuir, 1997. 13: p. 4948-4952.
13. Kjoniksen, A. L., C. Iversen, B. Nystrom, T. Nakken, and O. Palmgren, *Light scattering study of semidilute aqueous systems of chitosan and hydrophobically modified chitosans*. Macromolecules, 1998. 31: p. 8142-8148.
14. Uchegbu, I. F., A. G. Schätzlein, L. Tetley, A. I. Gray, J. Sludden, S. Siddique, and E. Mosha, *Polymeric chitosan-based vesicles for drug delivery*. Journal of Pharmacy and Pharmacology, 1998. 50: p. 453-8.
15. Wang, W., A. M. McConaghy, L. Tetley, and I. F. Uchegbu, *Controls on polymer molecular weight may be used to control the size of palmitoyl glycol chitosan polymeric vesicles*. Langmuir, 2001. 17: p. 631-636.
16. Lee, K. Y., W. H. Jo, I. C. Kwon, Y. H. Kim, and S. Y. Jeong, *Physicochemical characteristics of self-aggregates of hydrophobically modified chitosans*. Langmuir, 1998. 14: p. 2329-2332.
17. Lee, K. Y., J. H. Kim, I. C. Kwon, and S. Y. Jeong, *Self-aggregates of deoxycholic acid modified chitosan as a novel carrier of adriamycin*. Colloid and Polymer Science, 2000. 278: p. 1216-1219.
18. Akiyoshi, K., S. Deguchi, N. Moriguchi, S. Yamaguchi, and J. Sunamoto, *Self-aggregates of hydrophobized polysaccharides in water, formation and characteristics of nanoparticles*. Macromolecules, 1993. 26: p. 3062-3068.
19. Akiyoshi, K., E. C. Kang, S. Kurumada, J. Sunamoto, T. Principi, and F. M. Winnik, *Controlled association of amphiphilic polymers in water: Thermosensitive nanoparticles formed by self-assembly of hydrophobically modified pullulans and poly(N-isopropylacrylamides)*. Macromolecules, 2000. 33: p. 3244-3249.
20. Landoll, L. M., *Surfactant soluble cellulose derivatives*. 1979.

21. Kumar, G., J. F. Bristow, P. J. Smith, and G. F. Payne, *Enzymatic gelation of the natural polymer chitosan*. Polymer, 2000. 41: p. 2157-2168.
22. Wesslen, K. B. and B. Wesslen, *Synthesis of amphiphilic amylose and starch derivatives*. Carbohydrate Polymers, 2002. 47: p. 303-311.
23. Zhang, J., R. Pelton, and L. Wagberg, *Aqueous biphase formation by mixtures of dextran and hydrophobically modified dextran*. Colloid and Polymer Science, 1998. 276: p. 476-482.
24. Kastner, U., H. Hoffmann, R. Donges, and R. Ehrler, *Hydrophobically and Cationically Modified Hydroxyethyl Cellulose and Their Interactions with Surfactants*. Colloids and Surfaces a-Physicochemical and Engineering Aspects, 1994. 82: p. 279-297.
25. Roberts, G. A. F. and F. A. Wood, *A study of the influence of structure on the effectiveness of chitosan as an antifelting treatment for wool*. Journal of Biotechnology, 2001. 89: p. 297-304.
26. Viswanathan, A., *Effect of degree of substitution of octenyl succinate starch on the emulsification activity on different oil phases*. Journal of Environmental Polymer Degradation, 1999. 7: p. 191-196.
27. Kim, Y. H., S. H. Gihm, and C. R. Park, *Structural characteristics of size controlled self aggregates of deoxycholic acid-modified chitosan and their application as a DNA delivery carrier*. Bioconjugate Chemistry, 2001. 12: p. 932-938.
28. Lapasin, R., L. DeLorenzi, S. Pricl, and G. Torriano, *Flow properties of hydroxypropyl guar gum and its long-chain hydrophobic derivatives*. Carbohydrate Polymers, 1995. 28: p. 195-202.
29. Wakita, M. and M. Hashimoto, *Bilayer Vesicle Formation of N-Octadecylchitosan*. Kobunshi Ronbunshu, 1995. 52: p. 589-593.
30. Domard, A., M. Rinaudo, and C. Terrassin, *New method for the quaternisation of chitosan*. International Journal of Biological Macromolecules, 1986. 8: p. 105-107.
31. Uchegbu, I. F., L. Sadiq, M. Arastoo, A. I. Gray, W. Wang, R. D. Waigh, and A. G. Schutzlein, *Quarternary ammonium palmitoyl glycol chitosan—a new polysoap for drug delivery*. International Journal of Pharmaceutics, 2001. 224: p. 185-199.
32. Kalyanasundaram, K. and J. K. Thomas, *Environmental effects on the vibronic band intensities in pyrene monomer fluorescence and the application to studies of micellar systems*. Journal of the American Chemical Society, 1977. 99: p. 2039-2044.
33. Freshney, R. I., *Culture of animal cells: a manual of basic technique*. 3rd ed. 1994, New York: Wiley-Liss. xxiv, 486.

The invention claimed is:

1. A solubilising carbohydrate polymer of average molecular weight of about 2-30 kD according to the following formula:

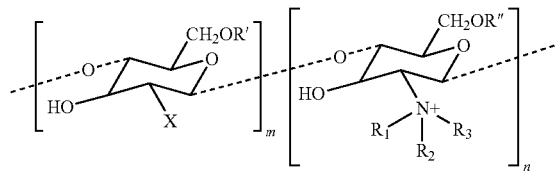

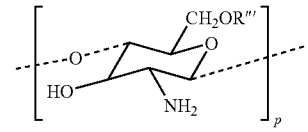

wherein m is 0.01% to 10.00%;
n is 0.01% to 99.98%;
p is 0.00% to 99.98%
X is any hydrophobic, linear, branched or cyclo form of an alkyl, alkenyl, alkynyl, aryl, amine, amide, alcohol or acyl group;
R', R", R''' are independently any linear, branched or cyclo form of an alkyl, alkenyl, alkynyl, aryl, acyl group, a sugar substituent selected from glucose, galactose, fructose and muramic acid, or oligo polyoxa $C_1$-$C_3$ alkylene units, optionally substituted with amine, amide or alcohol; and
$R_1$, $R_2$ and $R_3$ are independently any linear, branched, or cyclo forms of any alkyl, alkenyl, alkynyl, aryl or acyl group.

2. A solubilising carbohydrate polymer according to claim 1 wherein the m, n and p units form any arrangement in the solubilising carbohydrate polymer.

3. A solubilising carbohydrate polymer according to claim 1 wherein the arrangement of the m, n and p units are random or in a block copolymer form.

4. A solubilising carbohydrate polymer according to claim 3 wherein the block copolymer is mnpmnpmnp.

5. A method of forming a solubilising carbohydrate polymer according to claim 1 wherein the method comprises;
depolymerising a carbohydrate polymer to form depolymerised carbohydrate;
reacting the depolymerised carbohydrate with a first reactive compound to form hydrophobic side-groups on the carbohydrate backbone and thus form hydrophobically substituted depolymerised carbohydrate; and
adding a second reactive compound to the hydrophobically substituted depolymerised carbohydrate to quaternarise an amine group and thereby form the solubilising carbohydrate polymer.

6. A method according to claim 5 wherein the carbohydrate polymer is selected from the following: glycol chitosans, dextrans, alginic acids, starches, dextran and guar gums.

7. A carbohydrate polymer according to claim 1 and a pharmaceutically acceptable carrier.

8. A carbohydrate polymer according to claim 7 wherein the ratio of carbohydrate polymer to pharmaceutical acceptable carrier ranges from 0.05 wt. % to 10 wt. %.

9. A pharmaceutical composition comprising a carbohydrate polymer according to claim 1 and a drug.

10. A pharmaceutical composition according to claim 9 wherein the drug is selected from any of the following: prednisolone; cyclosporine; oestradiol, testosterone, drugs with multicyclic ring structures which lack polar groups etoposide.

11. A method of dissolving poorly soluble drugs in a carbohydrate polymer wherein the solubilising carbohydrate polymer is as defined in claim 1, whereby on dissolving a poorly soluble drug in the solubilising carbohydrate polymer a substantially clear solution is obtained.

12. A method according to claim 11 wherein the solubilising carbohydrate polymer is selected from any derivatives of the following: chitosans, dextrans, alginic acids, starches, dextran and guar gums.

13. A pharmaceutical composition according to claim 10 wherein the drug is paclitaxel.

14. A solubilising carbohydrate polymer according to claim 1, wherein X is selected from any of the following linear or branched or cyclo groups: $C_1$-$C_{30}$; $C_8$-$C_{24}$; or $C_{12}$-$C_{18}$.

15. A solubilising carbohydrate polymer according to claim 1, wherein X is $CH_3(CH_2)_{14}CONH$, or $CH_3(CH_2)_{15}NH$.

16. A solubilising carbohydrate polymer according to claim 1, wherein R', R" and R'" are independently any linear or branched or cyclo form of the following alkyl, alkenyl, alkynyl, aryl, or acyl groups: $C_1$-$C_{30}$; $C_1$-$C_{12}$; and $C_1$-$C_6$, optionally substituted with amine, amide or alcohol.

17. A solubilising carbohydrate polymer according to claim 1, wherein R', R" and R'" are $C_1$-$C_4$ linear glycol based groups.

18. A solubilising carbohydrate polymer according to claim 1, wherein R', R" and R'" are any of the following sugar substituents: glucose, galactose, fructose and muramic acid.

19. A solubilising carbohydrate polymer according to claim 1, wherein R', R" and R'" are oligo polyoxa $C_1$-$C_3$ alkylene units.

20. A solubilising carbohydrate polymer according to claim 1, wherein all of R', R" and R'" are $CH_2OCH_2CH_2OH$ or $CH_2CH_2OH$.

* * * * *